US009516141B2

(12) United States Patent
Dubois et al.

(10) Patent No.: US 9,516,141 B2
(45) Date of Patent: Dec. 6, 2016

(54) METHOD AND SYSTEM FOR PROCESSING MACHINE-TO-MACHINE SENSOR DATA

(71) Applicant: Verizon Patent and Licensing Inc., Basking Ridge, NJ (US)

(72) Inventors: Jean F. Dubois, Boothbay Harbor, ME (US); Patrick J. Moran, Shrewsbury, MA (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 598 days.

(21) Appl. No.: 14/013,861

(22) Filed: Aug. 29, 2013

(65) Prior Publication Data

US 2015/0067176 A1    Mar. 5, 2015

(51) Int. Cl.
*H04L 29/06* (2006.01)
*H04L 29/08* (2006.01)
*G06F 19/00* (2011.01)
*H04W 12/08* (2009.01)

(52) U.S. Cl.
CPC ........... *H04L 69/08* (2013.01); *G06F 19/3418* (2013.01); *H04L 65/102* (2013.01); *H04L 67/12* (2013.01); *H04L 63/20* (2013.01); *H04W 12/08* (2013.01)

(58) Field of Classification Search
CPC ..... H04L 69/08; H04L 65/102; H04L 67/12; H04L 63/20; G06F 19/3418; H04W 12/08
USPC ................................................. 709/227, 246
See application file for complete search history.

(56) References Cited

U.S. PATENT DOCUMENTS

| 6,363,431 | B1* | 3/2002 | Hammer | H04Q 3/0025 709/238 |
|---|---|---|---|---|
| 6,453,361 | B1* | 9/2002 | Morris | H04N 1/00132 709/203 |
| 6,873,620 | B1* | 3/2005 | Coveley | H04L 12/5835 370/395.31 |
| 7,194,252 | B1* | 3/2007 | Jordan, Jr. | H04L 12/5835 455/411 |
| 7,697,951 | B1* | 4/2010 | Martin | H04L 69/08 455/406 |
| 2003/0177440 | A1* | 9/2003 | Kegoya | G05B 19/042 715/273 |
| 2004/0015609 | A1* | 1/2004 | Brown | H04L 69/08 709/246 |
| 2004/0137915 | A1* | 7/2004 | Diener | H04L 41/0896 455/456.1 |
| 2005/0125491 | A1* | 6/2005 | Hasegawa | H04L 69/08 709/202 |
| 2005/0276278 | A1* | 12/2005 | Jung | H04L 69/18 370/466 |
| 2006/0037069 | A1* | 2/2006 | Fisher | H04L 67/02 726/11 |
| 2006/0111935 | A1* | 5/2006 | Bao | G06Q 50/22 705/2 |
| 2006/0155818 | A1* | 7/2006 | Odenwald | H04L 41/082 709/208 |
| 2007/0019656 | A1* | 1/2007 | Martin | H04L 65/4061 370/401 |
| 2009/0006522 | A1* | 1/2009 | Kim | H04L 29/12113 709/201 |
| 2009/0088605 | A1* | 4/2009 | Ross | A61B 5/0002 600/300 |

(Continued)

FOREIGN PATENT DOCUMENTS

JP    2006217704 A  *  8/2006
JP    2006323440 A  *  11/2006

(Continued)

*Primary Examiner* — Kostas Katsikis

(57) ABSTRACT

An approach is described for registering a plurality of gateway devices to a sensor platform operated by a service provider, detecting at the gateway devices, one or more sensors from a personal area network of a subscriber, determining corresponding identifiers of the sensors, collecting data from the sensors over one or more coordinated personal area networks, and designating each of a plurality of agents to process the collected data for local analysis and acting on this analysis, wherein the agents are configured to communicate with other agents.

22 Claims, 15 Drawing Sheets

(56) References Cited

U.S. PATENT DOCUMENTS

| | | | | |
|---|---|---|---|---|
| 2010/0315225 | A1* | 12/2010 | Teague | A61B 5/0024 340/539.12 |
| 2011/0066041 | A1* | 3/2011 | Pandia | A61B 5/113 600/484 |
| 2011/0137681 | A1* | 6/2011 | Lim | G06Q 10/10 705/3 |
| 2012/0316726 | A1* | 12/2012 | Schroeck | H04L 67/125 701/32.7 |
| 2013/0297630 | A1* | 11/2013 | DeSanzo | H04L 67/125 707/756 |
| 2015/0310362 | A1* | 10/2015 | Huffman | G06Q 50/22 705/2 |
| 2015/0364027 | A1* | 12/2015 | Haupt | G01W 1/02 340/521 |

FOREIGN PATENT DOCUMENTS

| | | | | |
|---|---|---|---|---|
| JP | | 2009194892 | A * | 8/2009 |
| JP | | 4385959 | B2 * | 12/2009 |
| KR | | 20090000932 | A * | 1/2009 |
| KR | | 20130000025 | A * | 1/2013 |
| WO | WO | 2013163202 | A1 * | 10/2013 |

* cited by examiner

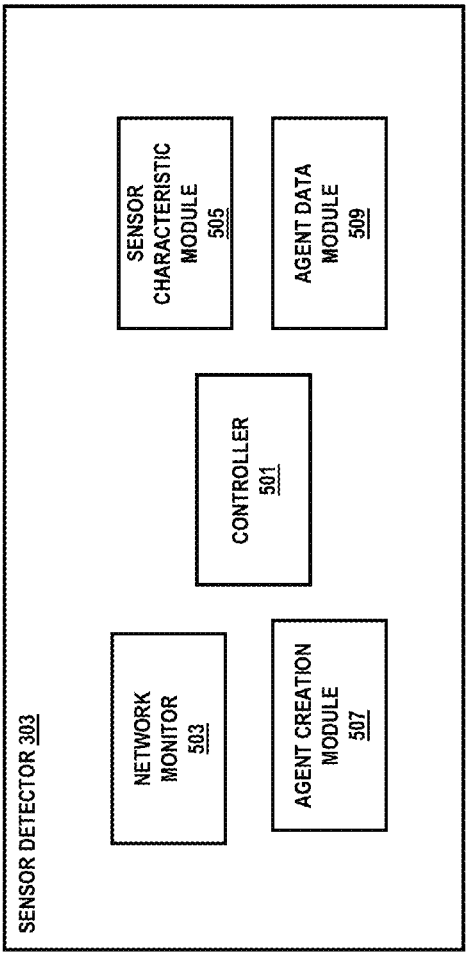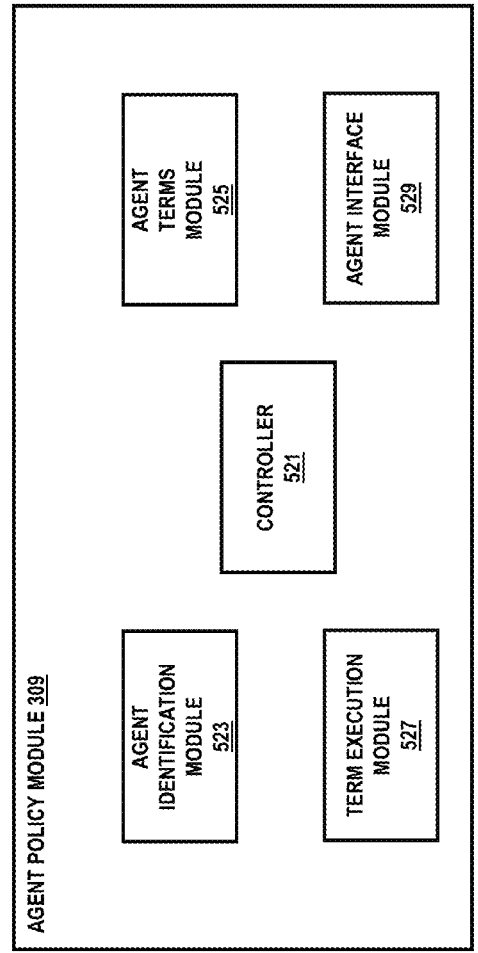
FIG. 5A
500
FIG. 5B
520

METHOD AND SYSTEM FOR PROCESSING MACHINE-TO-MACHINE SENSOR DATA

BACKGROUND INFORMATION

Numerous sensor devices are capable of collecting and transferring sensor data over a network. These devices typically operate independently with little to no coordination among them. The widespread practice of data collection systems using unique data formats particular to the systems further contributes to the isolation of sensor devices. As such, service providers and users face challenges in taking advantage of sensor data aggregated into a collective set. Manual attempts at coordinating various sensor devices and their data, if even possible, are time-consuming and inefficient.

Based on the foregoing, there is a need for automatically registering various sensor devices to a unified system to leverage sensor data collection from independent sources for, e.g., collective trend analysis.

BRIEF DESCRIPTION OF THE DRAWINGS

Various exemplary embodiments are illustrated by way of example, and not by way of limitation, in the figures of the accompanying drawings in which like reference numerals refer to similar elements and in which:

FIG. 5A is a diagram of a sensor detector capable of accessing sensors within a local or personal network to automatically ingest, process and manipulate sensor data, according to one embodiment;

FIG. 5B is a diagram of an agent policy module utilized in the policy engine of FIG. 1, according to one embodiment;

DESCRIPTION OF THE PREFERRED EMBODIMENT

An apparatus, method, and software for processing and configuring machine-to-machine sensor data and control is described. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the present invention.

Although the various exemplary embodiments are described with respect to processing and controlling log information for a telecommunications service provider, it is contemplated that these embodiments have applicability to systems operated by different organizations and to other operations wherein log information is collected.

Figure 1:
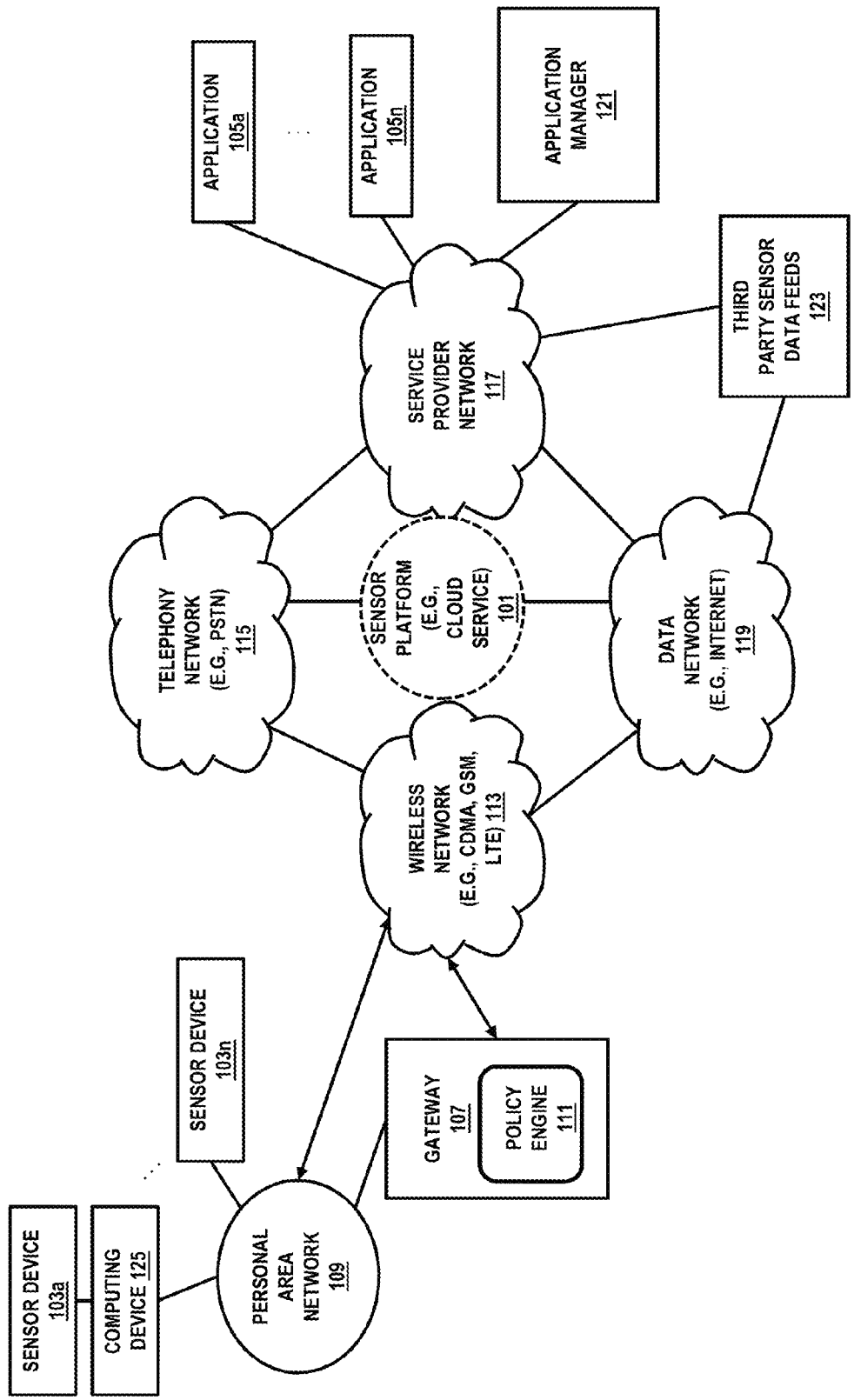
FIG. 1 is a diagram of a system capable of communicating with various sensor devices to collect their corresponding sensor data as part of a unified sensor data processing service, according to one embodiment.

FIG. 1 is a diagram of a system capable of communicating with various sensor devices to collect their corresponding sensor data as part of a unified sensor data processing service, according to one embodiment. For the purpose of illustration, system 100 employs, in certain embodiments, a sensor platform 101 that provides collective analysis for sensor data as well as for application data use, where analysis of application data use is enhanced. Sensor platform 101 also, in some embodiments, provides data conversion into one or more universal formats compatible with applications. Such capability in the sensor platform 101 supports vertical integration from a sensor device 103, to the sensor platform 101, to applications (and therefore businesses or service providers) 105*a*-105*n*.

In certain embodiments, vertical integration is functionally combining different components at various levels or forms of data acquisition under a centralized ecosystem created by sensor platform 101. Vertical integration provides seamless interaction between otherwise incompatible units. In one embodiment, vertical integration in system 100 involves the sensor platform 101 building unique capability to integrate sensor device 103 with applications 105*a*-105*n* via universal data formatting and device discovery. In other words, sensor device 103 are endpoints with embedded intelligence allowing the sensor device 103 to provide data to the sensor platform 101; and the sensor platform 101, in turn, contains intelligence specific to permitting applications 105*a*-105*n* to use data from the sensor platform 101. Sensor platform 101 is thus a central service relative to a collection of sensor devices that provides the means of building communications intelligence between sensor device 103, or direct sensors, and applications 105*a*-105*n*, all existing within a particular ecosystem. In one embodiment, the intelligence includes converting data into universal formats, for example, converting data obtained from sensor device 103a-103n into a universal format, then interfacing with applications 105a-105n that use data in the universal format. In one embodiment, sensor platform 101 may be implemented as part of a cloud service.

In one embodiment, gateway 107 transmit sensor data to the sensor platform 101 for the sensor platform 101 to convert into a universal data format. For gateway 107 to provide an interface between sensors 103 and the sensor platform 101, the sensor platform 101 may provide a gateway 107 with compatibility software to vertically integrate detected sensors 103 with the sensor platform 101. As used herein, a "sensor device" refers to a separate physical device that interfaces with a computing device 125 (as in sensor device 103a) or a single hardware that has the functionality of a sensor and a computer (e.g., a smart phone with a sensor application). It is noted that each of the sensor device 103a-103n may utilize a computing device 125 (e.g., mobile phone, laptop, or netbook, etc.) to communicate over a personal area network (PAN) 109 (or a local area network). In one embodiment, gateway 107 may be deployed as a customer premise device (e.g., a user gateway) to detect announcement signals from the sensor device 103a-103n, where the gateway 107 automatically begins collecting data from the sensor device 103a-103n. For example, the gateway may communicate with the sensor device 103a-103n and/or a computing device 125 associated with the sensor devices 103a-103n via a PAN 109, whereby the gateway 107 may continually scan the PAN 109 for sensor announcement signals.

Upon detecting sensor devices 103, the gateway 107 may prompt sensor devices 103 including itself to install software that vertically integrates the newly detected sensor devices 103 with sensor platform 101. In this way, sensor platform 101 may automatically receive data from the sensor devices 103 without prompting active user registration. The vertical integration between the sensor platform 101, gateway 107, and sensor device 103 may include end-to-end architecture functions to construct one or more building communication interfaces between these three components to allow data flow from sensor device 103 to the sensor platform 101. In one embodiment, the sensor platform 101 may register newly detected sensor devices 103 by pairing device identification with a user identification. For example, this pairing may be communicated to the gateway 107 using agent software. In one embodiment, this pairing may create a database record which is maintained in the sensor platform. The culmination of these database records may comprise an Identification System (IS). Registration of a database record in the IS corresponding to a detected sensor device 103a may complete the registration process for the new sensor device. Sensor platform 101 may then update the gateway 107 with a user identification to associate with the detected sensor 103a with the load of sensors 103 to pair.

According to one embodiment, after at least one sensor device 103a is automatically registered to a user and gateway 107, the policy engine 111 may facilitate communication among the various sensor devices 103a-103n within the gateway 107. The policy engine 111 that may enhance data processing and control before the data reaches the sensor platform 101 or other actuators by facilitating coordinated communication among the various sensor devices 103a-103n within the gateway 107. For example, the gateway 107 may be a user's mobile phone, while the sensor device 103a may be a glucose meter and the sensor device 103b may be a health bracelet. The policy engine 111 may then determine that the sensor device 103a may communicate with sensor device 103b and incorporate the glucose meter readings into health bracelet exercise trackers. In addition the policy engine may be configured on the fly to associate a short circuit control path to a nearby actuator or sensor. Nearby in this context refers to components that may have a relatively short communication path whose performance metrics are known by the policy engine and are selected by same to improve performance of the overall system. The gateway 107 may then transmit the resulting, processed data to the sensor platform 101 so that data in the sensor platform 101 is more readily usable by applications 105. According to one embodiment, the gateway 107 and policy engine 111 may adapt to future device formats such that these systems may be compatible with future sensor devices and their data formats.

In certain embodiments, gateway 107 may automatically register sensor device 103a-103n to the sensor platform 101. In one embodiment, the sensor platform 101 may prompt the gateway 107 to register or scan only for certain types of data capable of being converted to a universal data type. For example, a sensor platform 101 interfacing with healthcare-related applications may configure gateway 107 to scan only for sensor devices 103a-103b collecting in Food and Drug Administration (FDA)-compliant data. Once the devices are registered with the sensor platform 101, the sensor platform 101 may coordinate, for example, a publisher-subscriber communication forum among the various sensor device 103a-103n. There may exist a rendezvous point in this communication forum that is controlled by the policy engine through an access control list. This list may be configured, changed or tuned over the course of the data communication session or running time to provide enhanced security or other performance improvements.

By extension of the registration, gateway 107 may be designated as pertaining to a user and/or location. For example, the sensor platform 101 may recognize gateway 107 as "User 1's gateway" or as "Home." In one embodiment, the sensor platform 101 may include saving collected sensor data in a federated system that permits data from various sensors 103 to be accessed according to user or user device identification. The gateway 107 may receive and organize sensor data such that new sensors or sensor data feeds are pluggable, thereby preparing any new data detected within a given PAN 109 for processing in the sensor platform 101 regardless of sensor or data type. In other words, the gateway 107 may operate in a scalable, bus-type model that forms the interface between raw sensor data feeds and the sensor platform 101.

Additionally, the sensor platform 101 may map services and devices to a particular user so that collected sensor data is associated with at least one user. In this way, the sensor platform 101 may serve as a centralized service that retrieves and accesses user and device information, regardless of the user's location. Then, user services and/or applications may centrally access the data at the sensor platform 101 (provided that the sensor platform 101 verifies that the services and/or applications are authorized to access the user and/or device information). The sensor platform may carry information on behalf of other sensors assigned to other users through a sharing arrangement that may be preconfigured or configured at run time. When forwarding information or when sending PAN information the sensor platform may need to digitally sign the data payload or portions of it to ensure a chain of evidence and provide traceability and authenticity for applications in certain markets. The sensor platform may be required to collect and report these signatures from time to time by the centralized server or other applications within the system.

Sensor platform 101 can also utilize third party sensor data feeds 123, or indirect sensors, which may include data that has been already collected and processed by third parties and/or data not directly associated with one or more users and/or devices; the feeds 123 may be used to supplement or augment the trend analyses. For example, the data feeds 123 can relate to environmental condition information (e.g., outdoor temperature, weather data, etc.) or other data that may be relevant.

As previously discussed, the sensor platform 101 may further provide vertical integration with applications 105 so that applications 105 may take advantage of the collective sensor data. In other words, sensor platform 101 may vertically integrate these applications 105 by determining data formats used by the applications 105 and converting collected sensor data to the data formats common among various applications 105. To this end, sensor platform 101 may include a data converter that converts raw sensor data into a universal format compatible with applications. In doing so, applications may tap into the data resources of system 100 without application providers needing to code separately for compatibility.

The popularity of user-related sensor devices 103a-103n (e.g., bracelets that can track exercise and sleep habits or mobile phones that utilize a pedometer application) has created consumer-friendly sensors for a wide range of services. For example, a user wanting to improve his health may acquire a pedometer to monitor the number of steps the user takes. As a sensor device, the pedometer may track the number of steps over a period of time (e.g., week or month), and the collected data is analyzed for upward and downward trends in the user's steps for the given period of time.

Vertical integration enables sensor devices to work in concert as data is fed into the common pool of sensor platform 101, wherein the collective data can be used beyond the particular sensor device's targeted purpose. For example, pedometers can collect activity data, while sleep sensors independently collect data on sleep quality, patterns, and cycles, despite correlations between exercise and sleep. Unaware of the interplay between this data, a user of both devices may not readily set up a common application to monitor the relationship between the data sets outside of a unified system. Vertical integration would enable the seamless interfacing of different sensor devices. For instance, sensor platform 101 may permit pedometer data to be analyzed in conjunction with sensors that track the user's quality of sleep. Additionally, this data may lend insight into marketing and business interests. For example, the data from sensor devices may identify the spending habits of users as to correlate health and fitness habits with product recommendations. Additionally, the system 100 may determine that collected metadata indicates a geographic concentration of particularly active people. The system 100 may then determine the information by analyzing data collected from mobile phone pedometers. Alternately, the system 100 may determine the concentration of active people through analysis of application usage of data, facilitated by providing conversion of data into a common data format. In one instance, fitness and marketing companies may then provide applications and plan marketing targets based on the collected metadata analysis. Various forms of this vertically integrated data may be used as part of the digital signature that is included by default in the metadata and collected as part of the notification process of the users interaction with the use of the data.

In another scenario, the sensor platform 101 may be deployed to improve healthcare professionals' examinations of patients. For instance, sensor devices 103 may constantly monitor the vital signs of a particular user. When the user visits his doctor, the doctor may ask about the user's health habits and form her own recordings of the user's health. Conventionally, the doctor's records are separate from the user's sensor devices' tracking, despite possible overlap between the data sets. Therefore, there is a clear lack of integration of systems and data under the traditional approaches. Alternatively, a healthcare company may subscribe to sensor data and metadata acquired from sensor devices that are registered to their clients in the sensor platform 101. After the sensor platform 101 collects and converts client sensor device data and metadata, applications of the healthcare company may download this data and metadata into their database(s). In certain situations that authenticity of the data may be used to develop a ranking of the data relative to the trust of the source or the trust of the delivery method. This authenticity allows the end user or end application to determine whether to discount or accredit the value of the data as the data is being received and or used. With this database, the healthcare company may respond to members' various health readings in real time or monitor client health statuses for insurance and payment purposes. When the same user's sensor devices are integrated into sensor platform 101, the user's healthcare professional may have access to the user's sensor data immediately before and during the user's medical examination. This data may provide more accurate recordings than what the user may be able to provide based on his subjective memory or impressions. In addition the system may perform an automated task that actuates a mechanism such as an audible alarm or mechanical pump for example that is required in order to intervene within a timeframe that is well defined relative to the known responsively of the entire system.

In another healthcare use case, the system 100 may link a blood pressure monitor sensor device 103a to sensor platform 101 so that corresponding healthcare applications may provide a particular service to the user. As such, the sensor platform 101 and/or user gateway 107 may detect blood pressure sensor 103a. It is noted that the blood pressure sensor 103a may be part of a wearable device, according one embodiment. The gateway 107 may extract data measurements from the blood pressure sensor device 103a and transfer the data to the sensor platform 101, whereby healthcare application 105a may deliver the data to the user's healthcare company. According to one embodiment, the user's blood pressure readings are routinely reported to and monitored by the healthcare company by way of application 105a by sensor platform 101. For example, if a user's blood pressure reaches a predetermined unhealthy range, the sensor platform 101 may notify the user as well as a designated user (e.g., user's family member) (based on profile information supplied by sensor platform's profile database) or the user's healthcare company via application 105a.

Furthermore, sensor platform 101 may provide aggregate trend analysis across multiple users. This aggregate trend analysis may be classified according to subject matter. For example, in addition to collecting one user's pedometer data, platform 101 may aggregate pedometer data from multiple pedometers and recognize patterns from the collective data set. In one instance, aggregate pedometer data may indicate that people tend to run in the morning or people tend to bike on the weekends. Furthermore, sensor platform 101 may analyze the pedometer data with respect to location information, e.g., global positioning system (GPS) coordinates.

Such analysis may reveal certain patterns that are not detectable by individual data sets, such as people who live in a relatively dry climate (e.g., southern Californians) tend to run outdoors or urbanites are inclined to run indoors. In this manner, platform 101 can pool the data in a central repository where data produced for the same subject can be analyzed collectively. Vertically integrated applications in system 100 may also provide the sensor platform with more input to analyze. For example, the system 100 may include application usage of sensor data in its analysis.

Also, users may initiate uploading of sensor data to computing devices and social networking groups, for further analysis or to compare personal measurements against that of other users. For instance, users may subscribe to groups whose members encourage one another to meet fitness goals by comparing data to predetermined threshold values. Therefore, popular usage creates a data intensive environment where users and applications independently create prolific sources of data.

For illustrative purposes, the networks 113-119 may be any suitable wireline and/or wireless network, and be managed by one or more service providers. For example, telephony network 115 may include a circuit-switched network, such as the public switched telephone network (PSTN), an integrated services digital network (ISDN), a private branch exchange (PBX), or other like network. Wireless network 113 may employ various technologies including, for example, code division multiple access (CDMA), enhanced data rates for global evolution (EDGE), general packet radio service (GPRS), mobile ad hoc network (MANET), global system for mobile communications (GSM), 4G long-term evolution (LTE), Internet protocol multimedia subsystem (IMS), universal mobile telecommunications system (UMTS), etc., as well as any other suitable wireless medium, e.g., microwave access (WiMAX), wireless fidelity (WiFi), satellite, and the like. Meanwhile, data network 119 may be any local area network (LAN), metropolitan area network (MAN), wide area network (WAN), the Internet, or any other suitable packet-switched network, such as a commercially owned, proprietary packet-switched network, such as a proprietary cable or fiber-optic network.

Although depicted as separate entities, networks 113-119 may be completely or partially contained within one another, or may embody one or more of the aforementioned infrastructures. For instance, the service provider network 117 may embody circuit-switched and/or packet-switched networks that include facilities to provide for transport of circuit-switched and/or packet-based communications. It is further contemplated that networks 113-119 may include components and facilities to provide for signaling and/or bearer communications between the various components or facilities of system 100. In this manner, networks 113-119 may embody or include portions of a signaling system 7 (SS7) network, or other suitable infrastructure to support control and signaling functions. In addition the system may operate as separate parts that rendezvous and synchronize periodically to form a larger system with similar characteristics.

According to exemplary embodiments, end user devices (not shown) may be utilized to communicate over system 100 and may include any customer premise equipment (CPE) capable of sending and/or receiving information over one or more of networks 113-119. For instance, voice terminal may be any suitable plain old telephone service (POTS) device, facsimile machine, etc., whereas mobile device (or terminal) may be any cellular phone, radiophone, satellite phone, smart phone, wireless phone, or any other suitable mobile device, such as a personal digital assistant (PDA), pocket personal computer, tablet, customized hardware, etc. Further, computing device may be any suitable computing device, such as a VoIP phone, skinny client control protocol (SCCP) phone, session initiation protocol (SIP) phone, IP phone, personal computer, softphone, workstation, terminal, server, etc.

System 100 is additionally detailed in co-pending application, entitled, "Method and System of Machine-To-Machine Vertical Integration with Publisher-Subscriber Architecture," which is incorporated herein by reference in its entirety.

Figure 2:
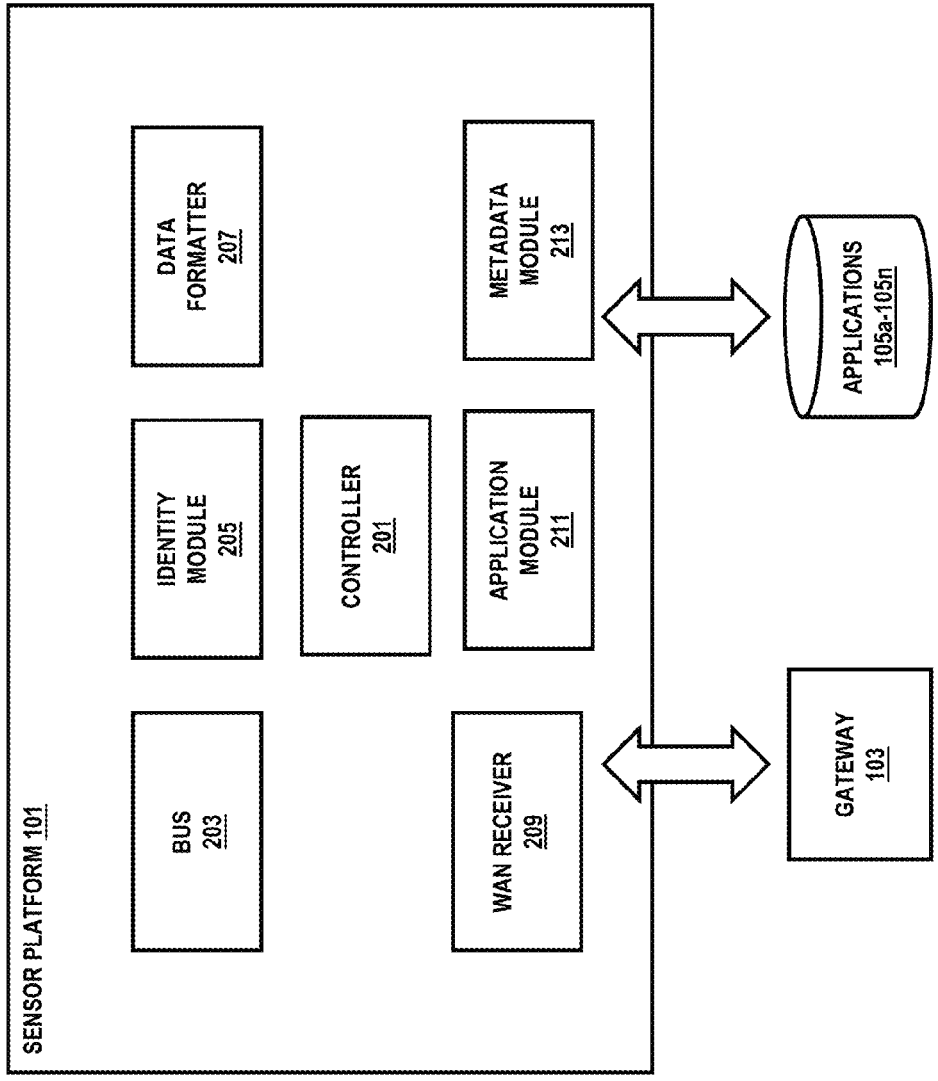
FIG. 2 is a diagram of a sensor platform capable of registering various sensor devices and receiving data intelligently, according to one embodiment.

FIG. 2 is a diagram of a sensor platform capable of registering various sensor devices and receiving data intelligently, according to one embodiment. The sensor platform 101 contains a controller 201, bus 203, identity module 205, data formatter 207, WAN receiver 209, application module 211, and metadata module 213. The sensor platform 101 may communicate with the gateway 107 to receive sensor data and convey the data to applications 105a-105n. In one embodiment, the sensor platform 101 may process the data to facilitate use by the applications 105a-105n. The gateway 107 may supply the sensor platform 101 with data and metadata from various sensor device 103a-103n.

The controller 201 performs control logic functions and facilitates coordination among the other components of sensor platform 101. In one embodiment, the bus 203 is a communication vehicle that transmits data and metadata among the gateway 107, applications 105a-105n, and all the various components within the sensor platform 101. The identity module 205 may register new user device and gateway pairs and store the information of current user device gateway pairs. An example embodiment of the identity module 205 may include a Universal Identification System (UIS) to provide assurance of associations between users and user devices, as well as security for transmitted sensor data. The UIS is a security application that facilitates strong authentication to web sites, applications, and networks by providing access only after providing a registered UIS identity. According to one embodiment, the UIS registration process may provide further security by requiring an activation code. Registration and authentication may occur several times over the course of the data acquisition events without the applications being disrupted from their normal operation. This authentication may be controlled by a proxy mechanism which is part of the sensor platform.

The data formatter 207 may receive data in various formats and convert this data into a universal format usable in applications 105a-105n. The data formatter 207 may have a different connector for different types of data streams. According to one embodiment, the data formatter 207 may include one connector dedicated to a sensor data stream and another connector dedicated to a video data stream. Each of these connectors may feed into a respective formatter depending on the original data format. Once the data formatter 207 converts the data feeds into a universal format, a stream controller may then provide the converted data and metadata into a connector that feeds the newly formatted data onto the bus 203. Bus 203 may subsequently distribute the converted data to the applications 105a-105n. Additional examples of data formatters are explained with respect to FIG. 3B and FIG. 11.

The WAN receiver 209 may contain both direct and indirect receiver components that accept data from both direct and indirect sensor devices though the bus 203. The application module 211 may manage the various applications which downloads and monitors the data from the sensor platform 101, tracking applications that fall to misuse and allotting system resources based on application activity. The metadata module 213 may store and manage trend metadata that attaches to the data sent from the various sensor device 103a-103n and third party sensor data feeds 123.

Figure 3:
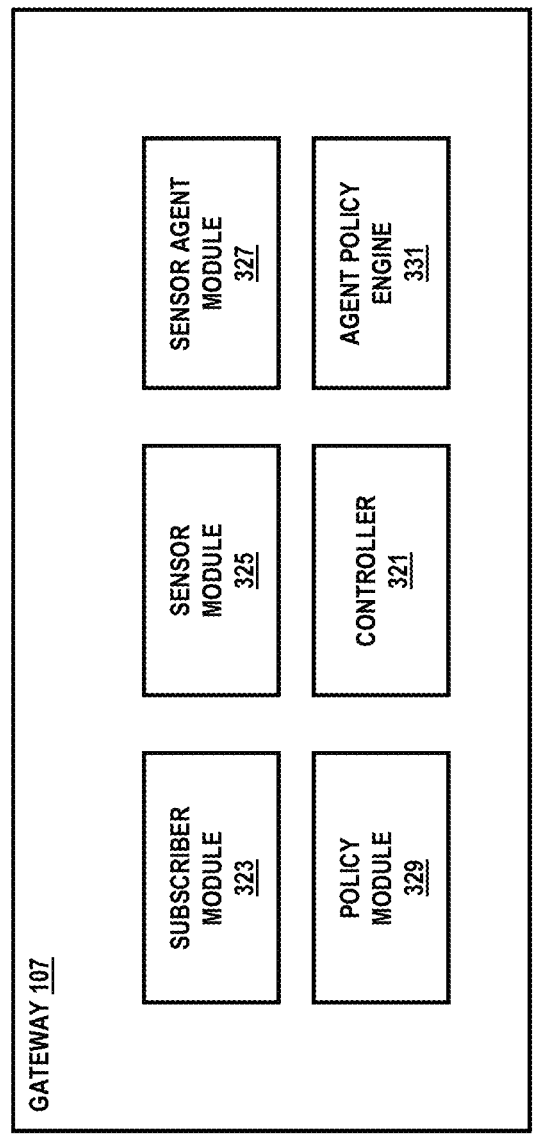
FIG. 3 is a diagram of a gateway capable of extracting sensor data and delivering the data to a sensor platform, according to one embodiment.

FIG. 3 is a diagram of a gateway capable of extracting sensor data and delivering the data to a sensor platform. Gateway 107 may comprise of computing hardware (such as described with respect to FIG. 15), as well as include one or more components configured to execute the processes described herein for providing the sensor to cloud processing services of system 100. In one implementation, gateway 107 includes subscriber module 323, policy module 329, agent policy engine 331, controller 321, sensor agent module 327, and sensor module 325. Gateway 107 may also communicate with the WAN and PAN 109. While specific reference will be made to this particular implementation, it is also contemplated that gateway 107 may embody many forms and include multiple and/or alternative components. For example, it is contemplated that the components of gateway 107 may be combined, located in separate structures, or separate locations.

The controller 321 and sensor module 325 may be configured to determine the presence of one or more sensor devices in the PAN 109 network. The sensor module 325 and controller 321 may associate sensor devices 103a-103n found by subscriber module 323 and controller 321 in the PAN 109 with the user's account. Once the sensor device is associated with a user's account, this association may be communicated to sensor platform when the data is transmitted by way of networks 113-119, PAN 109, or WAN. It is contemplated that a single user account may be associated with multiple sensor devices within a single gateway device. According to one embodiment, the sensor data may be saved in the sensor platform's federated system according to the user account associations assigned to the data by the subscriber module 323 and controller 321. Sensor agent module 327 and controller 321 will log and track the various sensor agents in the PAN 109 network, as well as monitor these sensor agents' activity level, or lack thereof. According to one embodiment the subscriber module 323 and the controller 321 may create new sensor agents in one or more gateway devices thus providing redundant, federated data collection systems. According to another embodiment, the sensor agent module 327 may perform data conversion. For example, the sensor agent module 327 may convert the units for a thermostat from Fahrenheit to Celsius.

The policy module 329 may determine the various data communication levels among the sensor agents in one or more gateway devices. The policy module 329 may also determine the data communication that the sensor agents may engage in with the sensor platform through the networks 113-119, WAN, and PAN 109. The agent policy engine 331 and the controller 321 may facilitate organized and coordinated communication among the various PAN 109 sensor agents in the gateway device and the sensor platform and between gateway devices that are used to dynamically manage PAN networks over the course of the data collection event. This communication will allow each PAN 109 sensor agent autonomous communication flexibility within the gateway device with other PAN 109 gateway devices and the sensor platform. The agent policy engine 331 may be a medium of communication among the various PAN 109 sensor agents as dictated by policy module 329 and controller 321.

Figure 4:
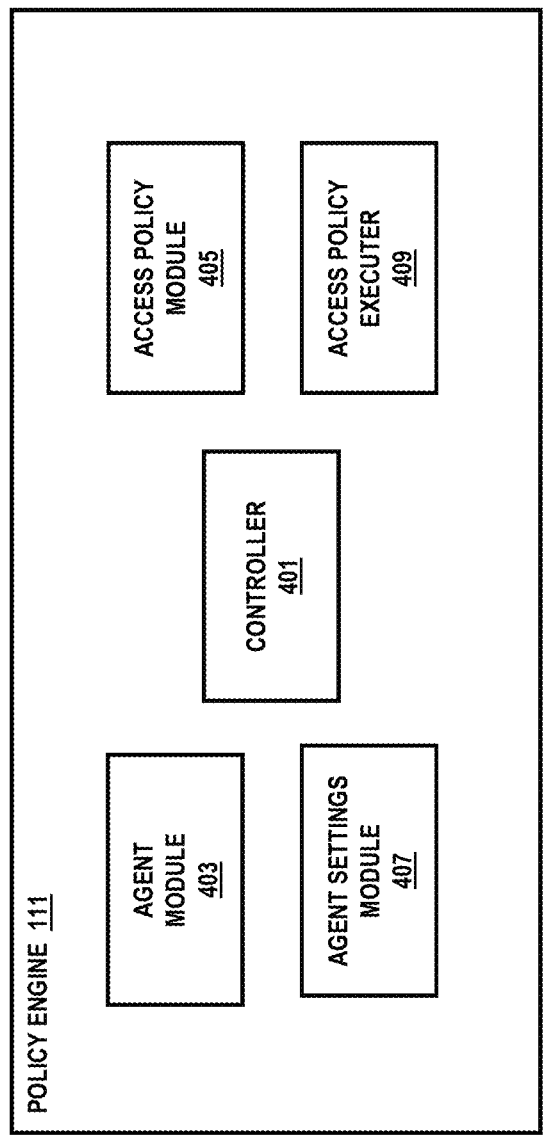
FIG. 4 is a diagram of a policy engine capable of controlling communications among the sensor agents, according to one embodiment.

FIG. 4 is a diagram of a policy engine capable of controlling communications among the sensor agents, according to one embodiment. Policy engine 111 may comprise computing hardware (such as described with respect to FIG. 14), as well as include one or more components (e.g., software, firmware, specialized hardware, or a combination thereof) configured to execute the processes described herein for providing the sensor to cloud processing services of system 100. In one implementation, policy engine 111 includes controller 401, agent module 403, access policy module 405, agent settings module 407, and access policy executer 409. Policy engine 111 may also communicate over a wide area network (WAN)(not shown), which may be formed by any combination of the networks 113-119. User devices and sensor devices 103 associated with user devices may access policy engine 111 via the gateway 107. While specific reference will be made to this particular implementation, it is also contemplated that policy engine 111 may embody many forms and include multiple and/or alternative components. For example, it is contemplated that the components of policy engine 111 may be combined, located in separate structures, or separate locations.

In one embodiment, the controller 401 and agent module 403 may be configured to determine the presence of one or more agents, including sensor agents. For example, the gateway 107 may include an agent application programming interface (API) that communicates with all the agents associated with a gateway 107. The controller 401 and agent module 403 may then interact with the API to determine the agents associated with a gateway 107. The access policy module 405 may contain the access policy. For example, access policy include an access control list (e.g., in template form) dictating possible communication access controls among sensor agents. For instance, the access policy may include a set of settings relating to access rights. The controller 401 and access policy module 405 may then maintain and update the access policy for access by other modules of the policy engine 111.

Then, the controller 401 and agent settings module 407 may determine each agent's control settings with respect to the access policy. For example, the agent policy may permit sensor agents to select access to other sensor agents that process, for example, sensor data relating to temperature. The controller 401 and agent settings module 407 may determine whether a given sensor agent, for example, sensor agent A, requests access to other agents that process temperature sensor data, or if other sensor agents that process temperature sensor data may communicate with sensor agent A. The controller 401 and access policy executer 409 may then translate the settings into a format that can be applied to the agent policy module 309. For example, if the agent settings module 407 dictates that sensor agent A may communicate with all sensor agents that process temperature sensor data, the access policy executer 409 may determine that sensor agents B, C, and F process temperature sensor data and translate the settings such that sensor agent A may communicate with sensor agents B, C, and F. By extension, the agent policy module 309 may set up a "chat room" interface for the sensor agents A, B, C, and F to communicate.

FIG. 5A is a diagram of a sensor detector capable of accessing sensors within a local or personal network and automatically obtaining sensor data, according to one embodiment. Sensor detector 303 may comprise computing hardware (such as described with respect to FIG. 14), as well as include one or more components (e.g., software, firmware, specialized hardware, or a combination thereof) configured to execute the processes described herein for providing the sensor to cloud processing services of system 100. In one implementation, sensor detector 303 includes controller 501, network monitor 503, sensor characteristic module 505, agent creation module 507, and agent data module 509. Sensor detector 303 may communicate with the platform 101 via any combination of networks 113-119 (which may be part of a wide area network (WAN)). User devices and sensor devices 103 associated with user devices may access sensor detector 303 via the gateway 107. While specific reference will be made to this particular implementation, it is also contemplated that sensor detector 303 may embody many forms and include multiple and/or alternative components. For example, it is contemplated that the components of sensor detector 303 may be combined, located in separate structures, or separate locations. In addition the sensor, sensor agent and components in the system may have a reputation that is modulated over time. This reputation may be carried with the data and attached to the various components such that other portions of the system are able to make a decentralized decision of the usefulness an applicability of the sensors and other parts to the application requirements at the time of data collection or later.

In one embodiment, the controller 501 and network monitor 503 may scan the PAN 109 surrounding the gateway 107 for new sensors. In one embodiment, sensors may include sensor announcers; for example, the controller 501 and network monitor 503 may be configured to pick up sensor announcer signals, where the controller 501 and network monitor 503 automatically register the sensors associated with the signals to a gateway 107. Then, the controller 501 and network monitor 503 may contact the sensor characteristic module 505 to determine the nature of the sensor data. In one embodiment, the agent creation module 507 may use the information given by the sensor characteristic module 505 to determine some useful processing of the sensor data. For instance, the sensor data may include temperature data (or other environmental data, such as humidity). The controller 501 and agent creation module 507 may create a sensor agent to process the temperature data in a way that may be useful for determining whether thermostat changes need to occur. For instance, the agent creation module 507 may create a sensor agent that translates the temperature from Celsius to Fahrenheit. For example, the controller 501 and agent creation module 507 may determine that applications 105a-105n include applications that use temperature data in the context of triggering thermostat changes. The controller 501 and agent creation module 507 may then create a sensor agent associated with one or more sensors that takes note when the incoming temperature sensor data falls out of a pre-configured range. The controller 501 and agent data module 509 may prepare and/or contain data as processed by the sensor agents. For instance, the incoming sensor data may be a number. The controller 501 and sensor characteristic module 505 may determine that the sensor data represents a temperature, whereupon the controller 501 and agent data module 509 may process the number such that it is a temperature in Fahrenheit and add the tags, "temperature" and "Fahrenheit" to the processed number.

FIG. 5B is a diagram of an agent policy module utilized in the policy engine of FIG. 1, according to one embodiment. Agent policy module 309 may comprise computing hardware (such as described with respect to FIG. 14), as well as include one or more components (e.g., software, firmware, specialized hardware, or a combination thereof) configured to execute the processes described herein for providing the sensor to cloud processing services of system 100. In one implementation, agent policy module 309 includes controller 521, agent identification module 523, agent terms module 525, term execution module 527, and agent interface module 529. User devices and sensor devices 103 associated with user devices may access the agent policy module 309 via the gateway 107 or directly via a WAN. While specific reference will be made to this particular implementation, it is also contemplated that agent policy module 309 may embody many forms and include multiple and/or alternative components. For example, it is contemplated that the components of the agent policy module 309 may be combined, located in separate structures, or separate locations.

In one embodiment, the agent policy module 309 may include an agent identification module 523 that identifies an agent to the policy engine 111. For example, the controller 521 may and agent identification module 523 may register a unique identifier associated with an agent. Alternately or in addition, the controller 521 and agent identification module 523 may identify agents according to sensors, devices, users, and/or sensor data associated with a given agent. Then, the controller 521 and agent terms module 525 may extract agent access control setting terms from the policy engine 111. For example, the controller 521 and agent terms module 525 may determine that a given agent A has setting terms that permit agent A to communicate with agent B. The controller 521 and term execution module 527 may then determine relevant terms for communication. For example, the controller 521 and term execution module 527 may contact both agent A and agent B to initiate interaction. In addition, the controller 521 and term execution module 527 may determine limitations within the setting terms. For instance, agent A's access terms may dictate that agent A permits communication with agent B for only a subset of data associated with agent A. The controller 521 and term execution module 527 may recognize this limitation and translate the term for the controller 521 and agent interface module 529 when the controller 521 and agent interface module 529 set up a communication forum in accordance with the terms. These terms may also be discovered locally based on the reputation of the various components in the system.

Figure 6:
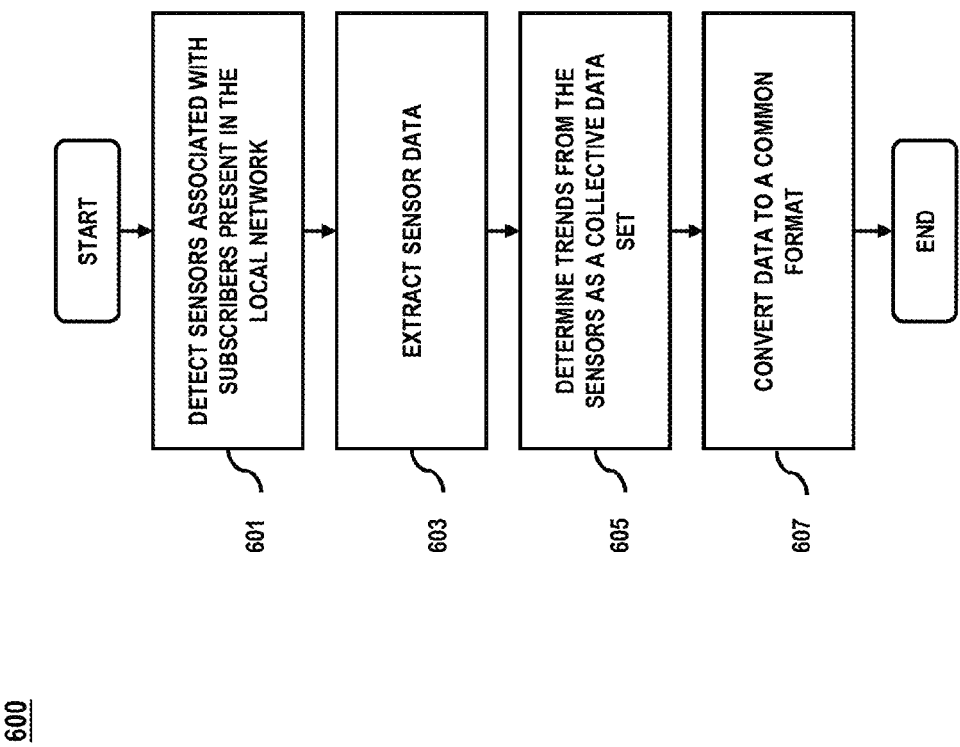
FIG. 6 is a flowchart of a process for acquiring sensor data to determine individual and collective trends, according to one embodiment.

FIG. 6 is a flowchart of a process for acquiring sensor data to determine individual and collective trends, according to one embodiment. For the purpose of explanation, this process is described as being implemented by controller 201 of sensor platform 101. Controller 201 may register multiple gateway devices (of which one is shown as gateway 107) to sensor platform 101 operated by a service provider. In step 601, the controller 201 may detect one or more sensors 103a-103n served by personal area network 109. Under this example, at least one of the sensors 103a-103n outputs data in a format different from other ones of the sensors 103a-103n.

The controller 201 may then determine corresponding identifiers of the sensors 103a-103n. According to one embodiment, the sensor platform 101 may contain a universal identification system (UIS), which associates users, their devices, and their gateway devices. The sensor platform 101 may communicate this association information from the UIS into the gateway 107 and controller 321, so that the gateway 107 and controller 321 may determine the identity of the sensors and the user in the PAN 109. Furthermore, the UIS may provide added security to the data transfer, where the sensor platform 101 may verify that sensor devices 103a-103n and/or gateway devices (one.g., gateway 107) communicating with the sensor platform 101 are authorized to do so. In step 603, the sensor platform 101 (specifically controller 201) may receive the data in the various formats, which may be proprietary to the respective sensors 103a-103n. According to one embodiment, gateway 107 can execute sensor agents corresponding to one or more sensor devices 103a-103n registered to the gateway 107. In step 605, the controller 321 may designate each of the agents to process the collected data for trend analysis. It is noted that the agents are configured to communicate with each other. In step 607, the sensor platform 101 and controller 201 may convert one of more of the corresponding data formats to a common format that can be utilized by multiple applications.

Figure 7:
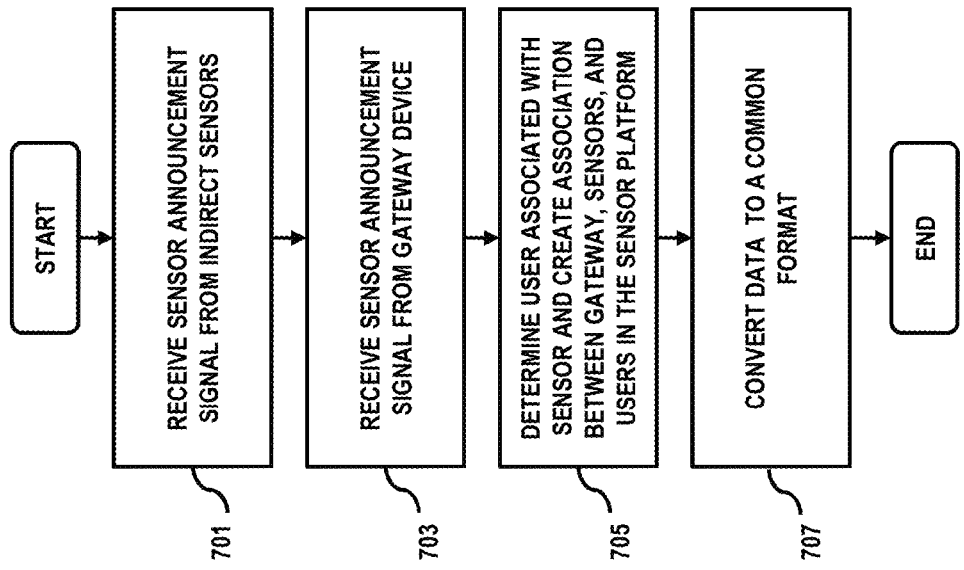
FIG. 7 is a flowchart of a process for identifying and grouping some sensors through a gateway, according to one embodiment.

FIG. 7 is a flowchart of a process for identifying and grouping some sensors through a gateway device, according to one embodiment. Within the system 100, controller 201 of the platform 101 or controller 321 of the gateway 107 may associate one or more of the sensor devices 103a-103n with one or more gateway devices. It is noted that the sensor devices 103a-103n can correspond to one or more users (that is, user accounts). In this example, controller 201 operates to provide the association among the devices 103a-103n. In step 701, the controller 201 may scan for signals from indirect sensors. Such sensors may communicate directly with the sensor platform 101 without an intermediary gateway device (e.g., utilize other communication paths). The controller 201 may then initiate the installation of an interfacing software in the indirect sensors before selectively registering them. This process can be largely mirrored in gateway device registration by controller 201. In step 703, the controller 201 may automatically detect the gateway devices that are a part of the service, and initiate installation of the interfacing software in the gateway devices before registering the gateway devices. In step 705, according to one embodiment, the controller 201 identifies the sensors, the gateway devices, as well a user account before establishing the association of these components with the user accounts. Once this association is completed, the sensor platform 101 may communicate such associations to the user account's gateway device. In step 707, data is received from the sensors (which may be indirect sensors) and the gateway devices, and then the data formats of such data can be converted, as needed, into a common (universal) format. This common format is compatible with multiple applications.

By way of example, when a new sensor device is introduced into a PAN 109 by a user (e.g., subscriber of the cloud service), the controller 201 may combine the new sensor device information and create an association with the user's account and its corresponding gateway device. Platform 101 can be configured to recognize any data that comes from this new device as data corresponding to that user's account. If there are multiple direct sensor devices, the controller 201 may allow for an exchange of data among the various sensor devices within the PAN 109. Thus, the new device may communicate with already registered devices within the PAN 109.

The platform 101 may perform data conversation and analytics from the collected data (on an individual sensor basis or as a collective data set from multiple sensors). As previously noted, indirect gateway devices, such as intelligent thermostats and scales with WiFi capabilities, can communicate directly with the platform 101 without traversing a gateway device.

Figure 8:
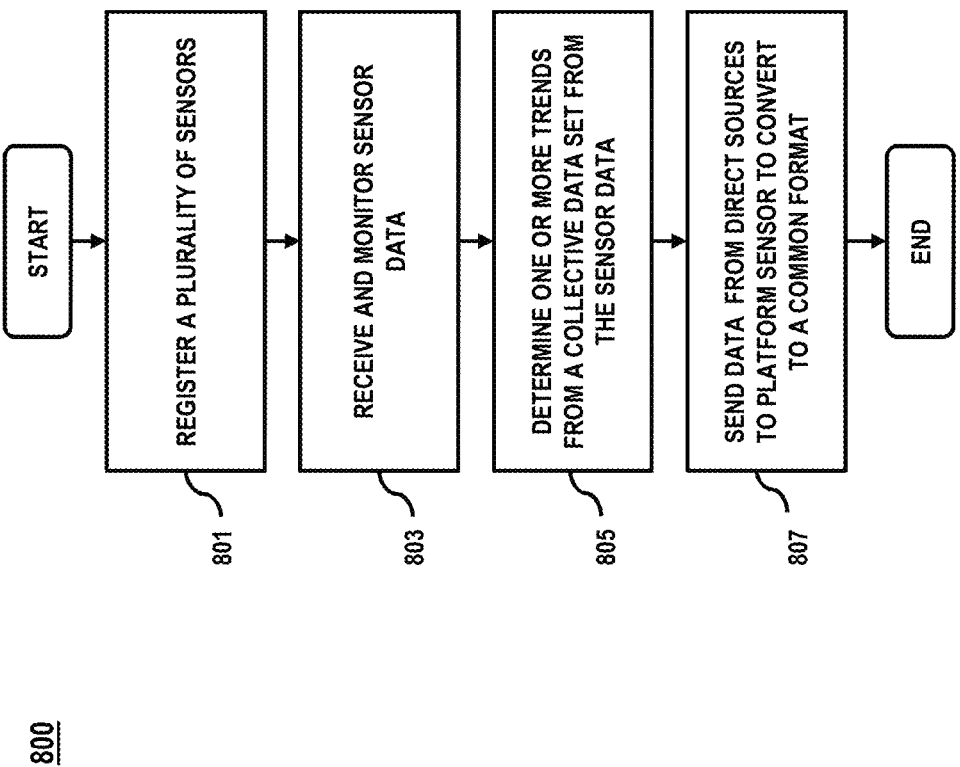
FIG. 8 is a flowchart of a process for collecting data from various sensor devices into a sensor platform and converting this data into a usable universal format, according to one embodiment.

FIG. 8 is a flowchart of a process for collecting data from various sensor devices into a sensor platform and converting this data into a usable universal format, according to one embodiment. In step 801, the process (which, in this example, is performed by sensor platform 101) detects one or more sensors 103a-103n. It is contemplated that a sensor (e.g., sensor 103a) can output data in a format different from another sensor (e.g., anyone of sensors 103b-103n).

As mentioned, the platform 101 (e.g., via of controller 321) may detect as subscribers, individual sensors, sensors via gateways associated with locations and/or users, service providers, or a combination thereof. In one embodiment, the subscribers may refer to users, devices, gateways, services, or a combination thereof. These subscribers may be direct, and thereby include sensors associated with users and/or devices; while indirect subscribers may include third parties associated with data feeds.

In step 803, the platform 101 may receive data from the sensors 103a-103n. According to one embodiment, the controller 321 of gateway 107 may monitor the data collection process and recognize any prolonged inactivity of a registered sensor device and remove the "inactive" sensor from the collection of sensor devices 103a-103n. From the monitoring, the gateway 107 may acquire the sensor data as a collective data set, which can then be used to determine one or more trends and tag the collective data set with metadata for the determined trends (step 805). In step 807, the gateway 107 may forward the data to sensor platform 101, which can then access whether conversion of the corresponding data formats into a common format for use by multiple applications.

Figure 9:
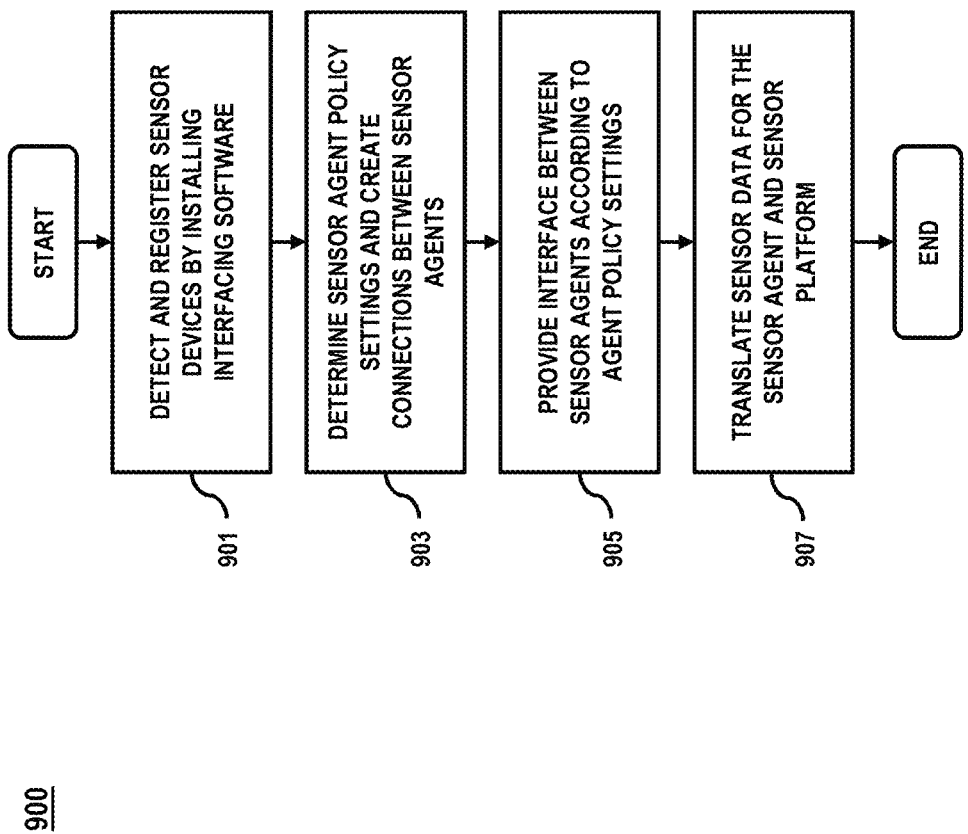
FIG. 9 is a flowchart of a process for discovering, registering, and managing several sensor devices within a gateway registered to a sensor platform, according to one embodiment.

FIG. 9 is a flowchart of a process for discovering, registering, and managing several sensor devices within a gateway device registered to a sensor platform, according to one embodiment. In one embodiment, this process can be executed by gateway 107 using controller 321. As shown, the process, per step 901, may automatically detect a direct sensors, selectively register the direct sensors, and install an interfacing software into the direct sensors. Next, in step 901, the controller 321 may collect the data in various formats from the sensors 103a-103n (which may include direct sensors and/or indirect sensors). In step 903, the controller 321 may receive, from the sensor agents, respective access settings associated with the agents. In step 905, the process can create an interface for communication among the agents based on the access settings. In one embodiment, each device registered to the gateway 107 in the PAN 109 has one or more corresponding sensor agents within the gateway 107. These sensor agents may act autonomously within the gateway 107. Each sensor agent, in certain embodiments, may communicate with other sensor agents by publishing to or subscribing from any of the other sensor agents within a chat room-style bus-model. The policy engine 111 within the gateway 107 can thus manage these publications and subscriptions for these sensor agents. Also gateways may maintain a record of historical changes such that the change trends can be discovered locally to assist with data collection management and rendezvous opportunities.

According to one embodiment, the interface may be a "chat room" or instant messaging session between agents in accordance with agent control access settings. In this "chat room," the controller 321 may determine one or more characteristics of the data and/or the agents. One or more access rules may be determined based on the characteristics relating to the communication among the agents; the policy engine 331 may be programmed or configured accordingly. In step 907, the sensor data for the corresponding sensor agent(s) as well as the sensor platform 101. That is, because of the variety of different sensor devices 103a-103n, data format conversion is performed to permit communication among the sensor agents and to enable the platform 101 to forward the converted data to a multitude of applications with different data requirements.

Figure 10:
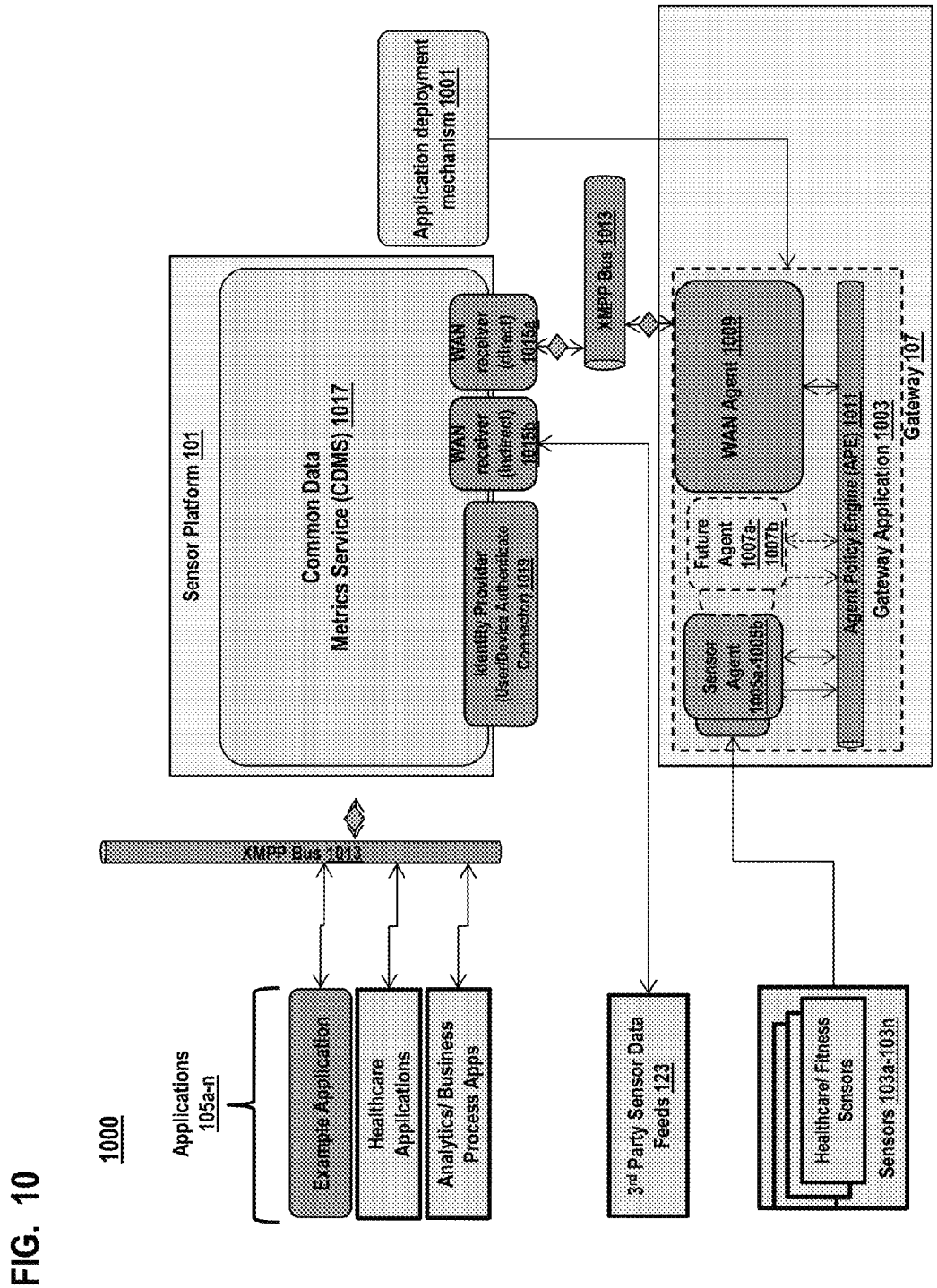
FIG. 10 is a diagram of a wireless environment where data from various sensors enters the sensor platform via a gateway, according to one embodiment.

FIG. 10 is a diagram of a wireless environment where data from various sensors enters the sensor platform via a gateway, according to one embodiment. According to one embodiment, sensors may include healthcare and fitness sensors which may communicate with one another through a PAN 109 in a gateway 107. The application deployment mechanism 1001 within the gateway 107 may automatically install the gateway device application 1003 onto the gateway 107. The application deployment mechanism 1001 may install and run a sensor platform gateway device application 1003 in the gateway 107. This sensor platform gateway device application 1003 may allow various sensor agents 1005a-1005b that transmit data from all the devices 103a-103n within the PAN 109 to communicate with one another and the sensor platform 101 in a unified and organized manner. The gateway device application 1003 also allows for the ability to plug in future sensor agents 1007a-1007b, and the ability to communicate with a WAN agent 1009. Each of these agents 1005-1009 are relatively autonomous and may have varying levels of communication with one another depending on their various policies. These policies contain the rules that dictate the levels of communication these agents 1005-1009 may have with one another. These various agents 1005-1009 may communicate with one another by way of the agent policy engine (APE) 1011. This APE 1011 is a pluggable bus-type system that functions as a chat room for all internetwork agents 1005-1009.

Figure 11:
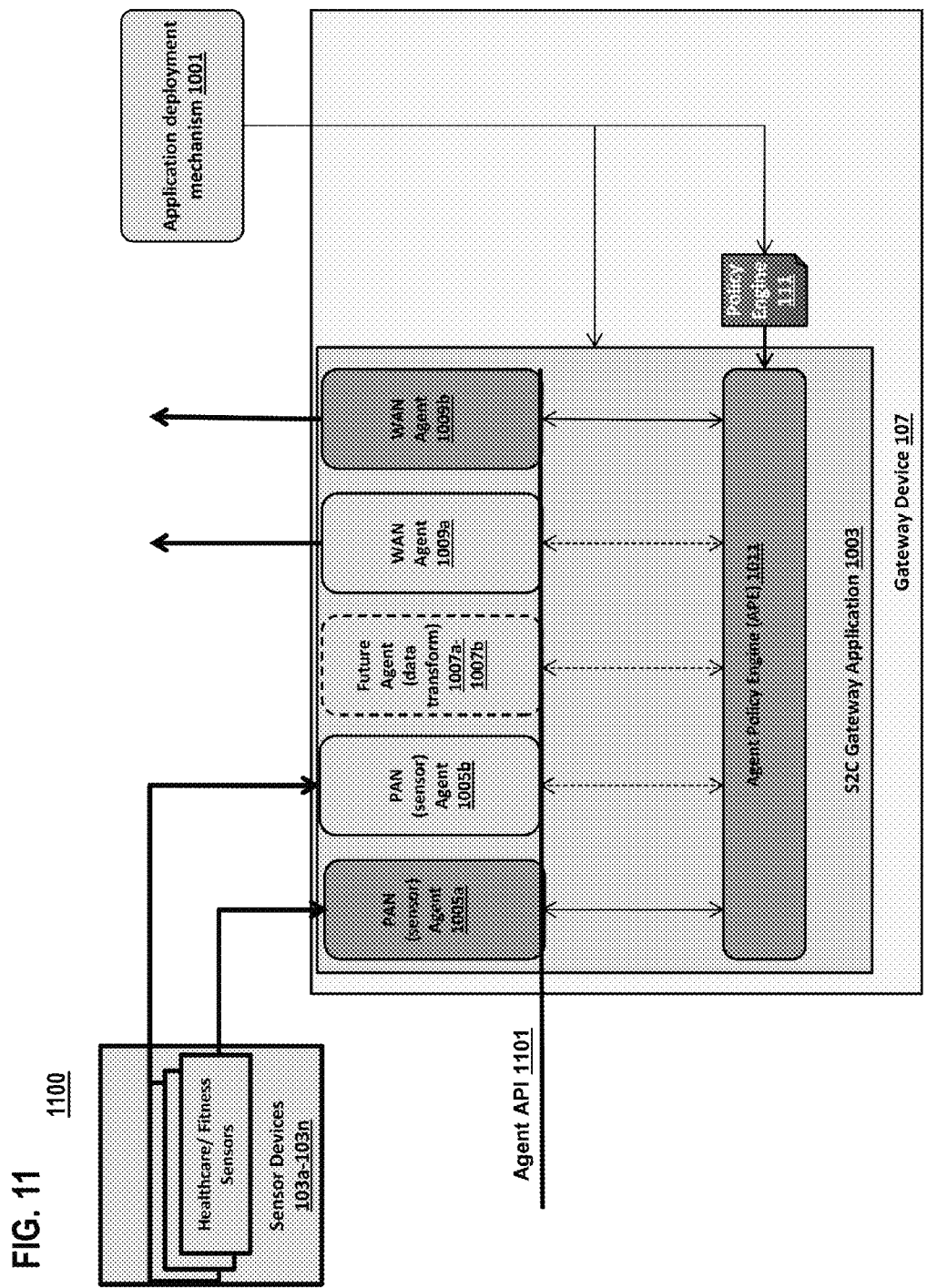
FIG. 11 is a diagram of a gateway used in the system of FIG. 1, according to one embodiment.

FIG. 11 is a diagram of a gateway device used in the system of FIG. 1. According to one embodiment, an application deployment mechanism 1001 may automatically install the gateway device application 1003 into the device gateway 107 and all of the sensor devices 103a-103n within the PAN 109. This installation process takes place in the background and demands no user interaction. According to one embodiment, this application process occurs upon registration of the device. According to another embodiment, this installation process may automatically take place in the background when the new sensor device 103a is introduced into the PAN 109, networks 113-119, or WAN.

The system components as described herein make the provisioning and commissioning of the sensors and other system components by various business entities, such as a fulfillment house, an integral part of the normal operation of data collection within the system. As such the assignment or reassignment of a user to one or more users is accomplished as a form of data collection: this instance being the collection and association of trust between an end user and the sensor. An example of the data collection is described below.

Figure 12:
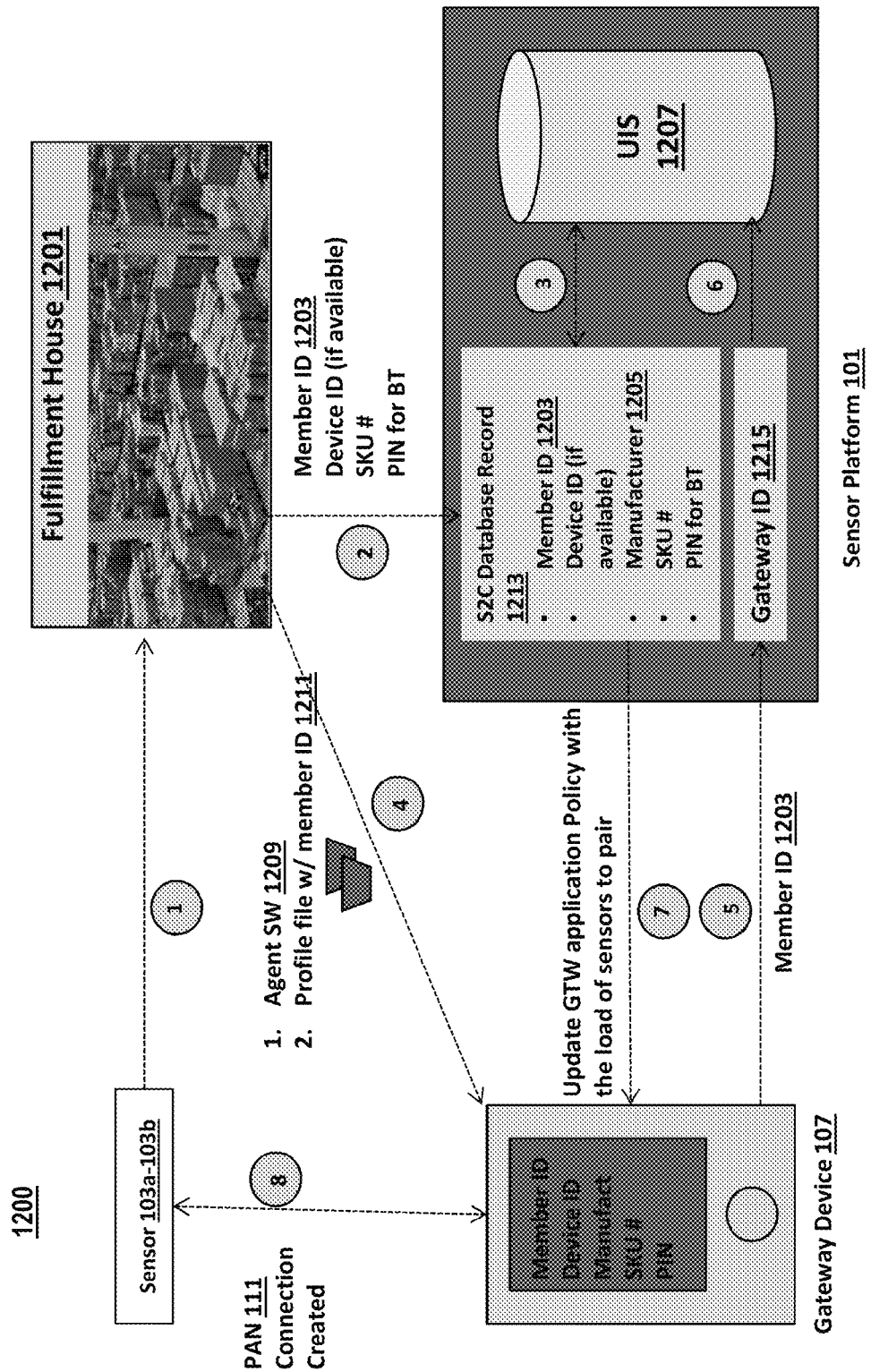
FIG. 12 is a diagram of a use case in which sensor devices are deployed in a fulfillment house, according to one embodiment.

FIG. 12 is a diagram of a use case in which sensor devices are deployed in a fulfillment house. According to one embodiment, for a direct sensor (e.g., anyone of devices 103a-103n), the process (step 1) may initiate upon detection of a sensor 103a by the gateway device application 1003. The fulfillment house 1201 pairs the device information with the user's member identification 1203. In step 2, this data is transmitted to the sensor platform 101 to add manufacturer information 1205 for the creation of a database record 1213. In step 3, the sensor platform 101 registers this database record 1213 with the universal identity system (UIS) 1207 in the sensor platform 101. In step 4, the agent software 1209 and the profile file with member identification 1203 for the user is created and connected with the gateway 107. The agent software 1209 and profile with member identification 1203 may be communicated to the gateway 107 through the PAN 109. In step 5, when the gateway 107 has paired with the member identification 1203 and communicates with the sensor platform 101, the sensor platform 101 uses this information and matches it with the database record 1213 to create gateway identification 1215 for this gateway 107. In step 6, the gateway identification 1215 and its gateway 107 and member pairing is registered in the UIS 1207. The UIS 1207 will match this gateway identification 1215 with its database record 1213. In step 7, the sensor platform 101 will update the gateway 107 with a policy engine 111 and all the potential additional sensor devices 103a-103n that have been registered to the member identification 1203. In step 8, the gateway 107 completes the PAN 109 connection upon reception of database record 1213 information from step 7 from the sensor platform 101.

According to one embodiment, the process (per step 1) begins with the fulfillment house 1201 pairing the sensor device 103a to a member identification 1203. In step 2, the fulfillment house 1201 will transmit this data to the sensor platform 101; where, in step 3, the manufacturer information 1205 is added and the database record 1213 is registered into the UIS 1207. Thus, the UIS 1207 allows for a federated system, which may support user mobility because the sensor platform 101 and UIS 1207 may always know which sensor devices 103a-103n and gateway 107 are linked with which member identification 1203 regardless of whether the user is in a certain location or using a personal area network. According to one embodiment, the sensor platform 101 may be capable of registering sensors devices 103a-103n and third party sensor data feeds 123 and collecting data from sensor devices 103a-103n and gateway 107 whether or not these sensor devices 103a-103n and third party sensor data feeds 123 are compliant with, for example, governmental regulations—e.g., Health Insurance Portability and Accountability Act (HIPAA) regulations.

Figure 13:
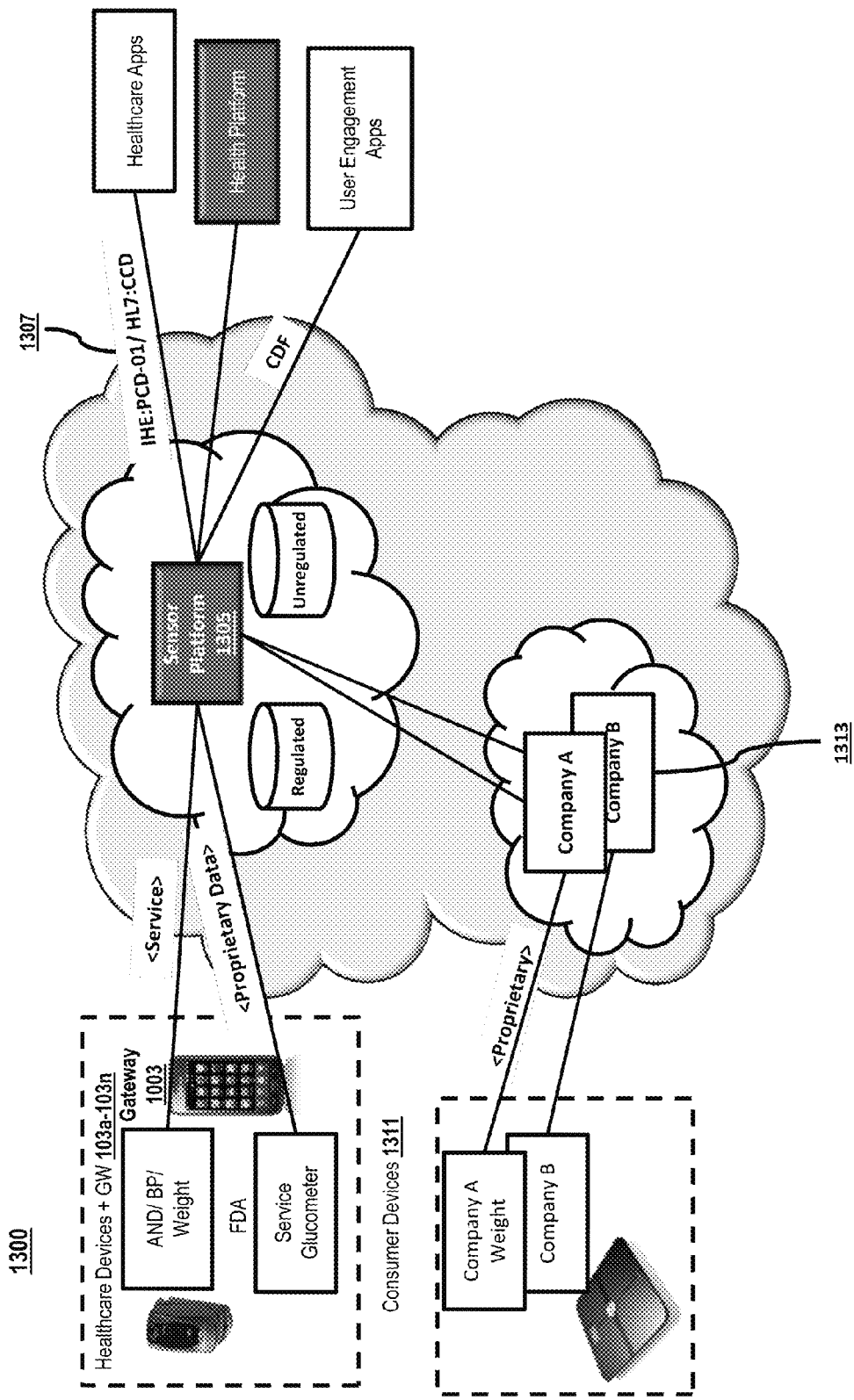
FIG. 13 is a diagram of a use case involving a system architecture for supporting health-related services, according to one embodiment.

FIG. 13 is a diagram of a use case involving a system architecture for supporting health-related services. For example, gateway 107 may automatically extract sensor data from sensors 103a-103n. In one scenario, the sensors 103a-103n may include healthcare-related sensors monitoring blood pressure, weight, blood glucose. The sensors 103a-103n may include both sensors that are compliant and sensors that are non-compliant with standards, such as Food and Drug Administration (FDA) standards. Furthermore, sensors 103a-103n may include sensors certified by particular healthcare solution such that the sensors 103a-103n are vertically integrated with the sensor platform and applications associated with the healthcare solution services.

Sensors 103a-103n may be associated with one or more locations, users, locations associated with users, etc. For example, Sensor 103a may be a mobile device belonging to a given user. For instance, user A's cell phone may act as a gateway 107, extracting and/or monitoring the blood pressure and weight or user A. The monitoring may be continuous or comprised of incremental measurements. In another example, gateway 107 may include a device designated as a "home gateway device" where the gateway 107 provides a sensor contact point at user A's "Home." The system 100 may associate each gateway 107 with its own collection of sensors 103a-103n. By way of example the "home gateway device" may contain data tags or signatures that provide certain additional features that are available for the sensors or agents that are within the "home PAN". These tags allow the sensors to collect information that is normally associated with home activities such as for example sleeping or personal home care. This may include transient information that relates to home care providers such as identification tags and identification activities.

In one embodiment, the gateway 107 may include sensor agents that process the sensor data and encode the data with various levels of security or identification tags. For example, the gateway 107 may send, to the sensor platform 1305, sensor data processed through the sensor agents, where the data is coded as proprietary data or data specific for the healthcare solution. In this way, the gateway 107 may permit data storage in the sensor platform 1305 without compromising data security. In one embodiment, the sensor platform 1305 may support various types of data formats. For example, the sensor platform 1305 may permit regulated and unregulated data, wherein regulated data may include HIPAA-compliant data and unregulated data may include all data. For instance, the sensor platform 1305 may detach data from user identifications associated with the data so that the data is anonymous. Such operations may include data anonymization or other encryption techniques.

In one embodiment, the sensor platform 1305 may also convert data into universal formats 1307 so that the data is more freely accessible by various applications 1309. For example, the common, universal formats 1307 may be contingent on the formats compatible with applications 1309. In one scenario, the sensor platform 1305 may convert data into the Common Data Format (CDF) for applications that can interface with CDF. In another scenario, the sensor platform 1305 may convert data into formats compatible with the Integrating the Healthcare Enterprise (IHE) and/or Health Level 7 (HL7) where applications relate to healthcare. In yet another scenario, the sensor platform 1305 may create its own universal format 1307 depending on the needs of applications involved with system 100.

In one embodiment, the sensor platform 1305 also receives data from third party sensor data feeds. For example, the sensors 103a-103n may provide direct connections to the sensor platform 1305 via registered gateway 107, whereas the third party sensor data feeds 1311 may include indirect connections to the sensor platform 1305. In one instance, the third party sensor data feed 1311 may not be associated with particular users or user devices. The third party sensor data feeds may include sensor data from, for example, consumer devices. The data for this type of case then, may be associated with a particular manufacturer, vendor, and/or company. For example, a Company A scale may transmit a third party sensor data feed 1311 to sensor platform 1305. In one case, the third party sensor data feed 1311 may first transmit the third party sensor data to a third party sensor agent 1313 for processing prior to sending the data to the sensor platform 1305. In another instance a particular vendor or manufacturer may supply a sensor that must be used within a defined time period that might represent a freshness sensor on a consumable product. The freshness data may be transported within the sensor platform and share the same data feed and be coupled to the user identification. The sensor agent may detect an anomalous condition and prevent the dispensing or signal an alarm that can be acted upon within a smaller component of the sensor platform.

The processes described herein for processing machine-to-machine sensor data may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 14:
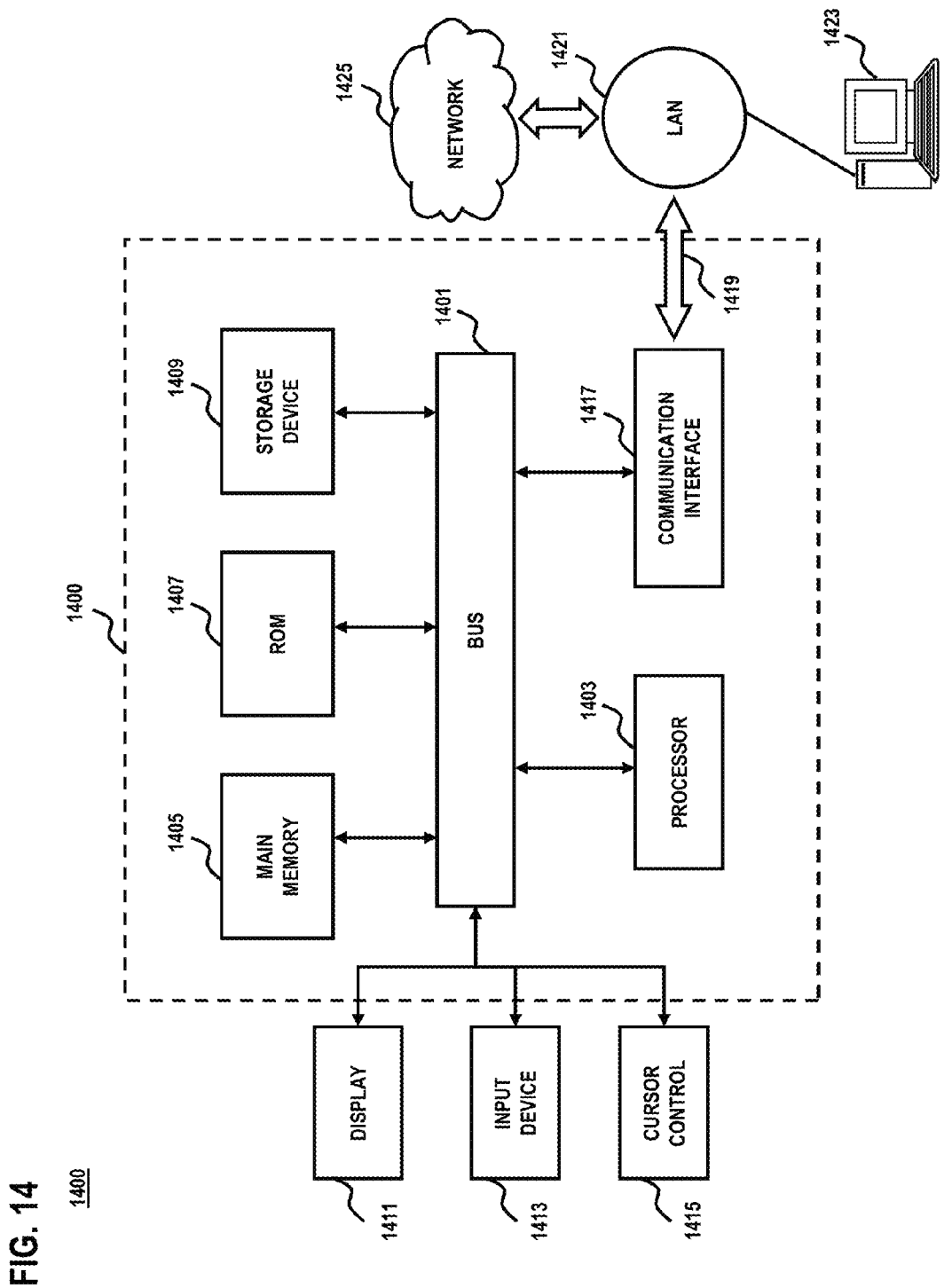
FIG. 14 is a diagram of a computer system that can be used to implement various embodiments.

FIG. 14 is a diagram of a computer system that can be used to implement various embodiments. The computer system 1400 includes a bus 1401 or other communication mechanism for communicating information and a processor 1403 coupled to the bus 1401 for processing information. The computer system 1400 also includes main memory 1405, such as a random access memory (RAM) or other dynamic storage device, coupled to the bus 1401 for storing information and instructions to be executed by the processor 1403. Main memory 1405 can also be used for storing temporary variables or other intermediate information during execution of instructions by the processor 1403. The computer system 1400 may further include a read only memory (ROM) 1407 or other static storage device coupled to the bus 1401 for storing static information and instructions for the processor 1403. A storage device 1409, such as a magnetic disk or optical disk, is coupled to the bus 1401 for persistently storing information and instructions.

The computer system 1400 may be coupled via the bus 1401 to a display 1411, such as a cathode ray tube (CRT), liquid crystal display, active matrix display, or plasma display, for displaying information to a computer user. An input device 1413, such as a keyboard including alphanumeric and other keys, is coupled to the bus 1401 for communicating information and command selections to the processor 1403. Another type of user input device is a cursor control 1415, such as a mouse, a trackball, or cursor direction keys, for communicating direction information and command selections to the processor 1403 and for controlling cursor movement on the display 1411.

According to an exemplary embodiment, the processes described herein are performed by the computer system 1400, in response to the processor 1403 executing an arrangement of instructions contained in main memory 1405. Such instructions can be read into main memory 1405 from another computer-readable medium, such as the storage device 1409. Execution of the arrangement of instructions contained in main memory 1405 causes the processor 1403 to perform the process steps described herein. One or more processors in a multi-processing arrangement may also be employed to execute the instructions contained in main memory 1405. In alternative embodiments, hard-wired circuitry may be used in place of or in combination with software instructions to implement exemplary embodiments. Thus, exemplary embodiments are not limited to any specific combination of hardware circuitry and software.

The computer system 1400 also includes a communication interface 1417 coupled to bus 1401. The communication interface 1417 provides a two-way data communication coupling to a network link 1419 connected to a local network 1421. For example, the communication interface 1417 may be a digital subscriber line (DSL) card or modem, an integrated services digital network (ISDN) card, a cable modem, a telephone modem, or any other communication interface to provide a data communication connection to a corresponding type of communication line. As another example, communication interface 1417 may be a local area network (LAN) card (e.g. for Ethernet™ or an Asynchronous Transfer Mode (ATM) network) to provide a data communication connection to a compatible LAN. Wireless links can also be implemented. In any such implementation, communication interface 1417 sends and receives electrical, electromagnetic, or optical signals that carry digital data streams representing various types of information. Further, the communication interface 1417 can include peripheral interface devices, such as a Universal Serial Bus (USB) interface, a PCMCIA (Personal Computer Memory Card International Association) interface, etc. Although a single communication interface 1417 is depicted in FIG. 14, multiple communication interfaces can also be employed.

The network link 1419 typically provides data communication through one or more networks to other data devices. For example, the network link 1419 may provide a connection through local network 1421 to a host computer 1423, which has connectivity to a network 1425 (e.g. a wide area network (WAN) or the global packet data communication network now commonly referred to as the "Internet") or to data equipment operated by a service provider. The local network 1421 and the network 1425 both use electrical, electromagnetic, or optical signals to convey information and instructions. The signals through the various networks and the signals on the network link 1419 and through the communication interface 1417, which communicate digital data with the computer system 1400, are exemplary forms of carrier waves bearing the information and instructions.

The computer system 1400 can send messages and receive data, including program code, through the network(s), the network link 1419, and the communication interface 1417. In the Internet example, a server (not shown) might transmit requested code belonging to an application program for implementing an exemplary embodiment through the network 1425, the local network 1421 and the communication interface 1417. The processor 1403 may execute the transmitted code while being received and/or store the code in the storage device 1409, or other non-volatile storage for later execution. In this manner, the computer system 1000 may obtain application code in the form of a carrier wave.

The term "computer-readable medium" as used herein refers to any medium that participates in providing instructions to the processor 1403 for execution. Such a medium may take many forms, including but not limited to non-volatile media, volatile media, and transmission media. Non-volatile media include, for example, optical or magnetic disks, such as the storage device 1409. Volatile media include dynamic memory, such as main memory 1405. Transmission media include coaxial cables, copper wire and fiber optics, including the wires that comprise the bus 1401. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read. In certain cases the computer readable media may include an unknown physical component wherein the information is uniquely defined by a special digital unique identifier and is available through multiple physical channels either simultaneously or exclusively.

Various forms of computer-readable media may be involved in providing instructions to a processor for execution. For example, the instructions for carrying out at least part of the exemplary embodiments may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

Figure 15:
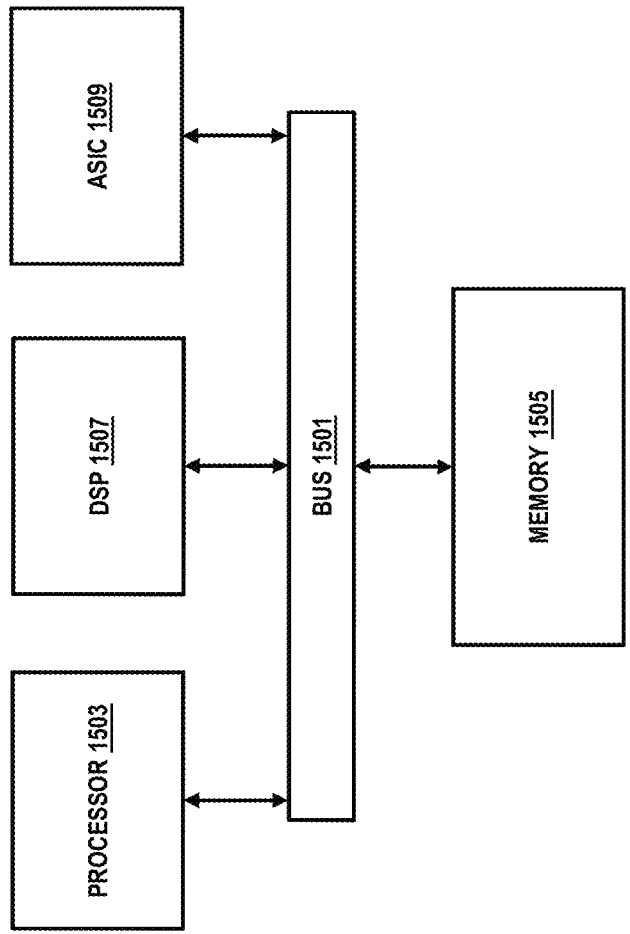
FIG. 15 is a diagram of a chip set upon which an embodiment of the invention may be implemented, according to one embodiment.

FIG. 15 is a diagram of a chip set upon which an embodiment of the invention may be implemented. Chip set 1500 is programmed to process machine-to-machine data as described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1500, or a portion thereof, constitutes a means for performing one or more steps of FIGS. 6-9.

In one embodiment, the chip set 1500 includes a communication mechanism such as a bus 1501 for passing information among the components of the chip set 1500. A processor 1503 has connectivity to the bus 1501 to execute instructions and process information stored in, for example, a memory 1505. The processor 1503 may include one or more processing cores with each core configured to perform independently. A multi-core processor enables multiprocessing within a single physical package. Examples of a multi-core processor include two, four, eight, or greater numbers of processing cores. Alternatively or in addition, the processor 1503 may include one or more microprocessors configured in tandem via the bus 1501 to enable independent execution of instructions, pipelining, and multithreading. The processor 1503 may also be accompanied with one or more specialized components to perform certain processing functions and tasks such as one or more digital signal processors (DSP) 1507, or one or more application-specific integrated circuits (ASIC) 1509. A DSP 1507 typically is configured to process real-world signals (e.g., sound) in real time independently of the processor 1503. Similarly, an ASIC 1509 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1503 and accompanying components have connectivity to the memory 1505 via the bus 1501. The memory 1505 includes both dynamic memory (e.g., RAM, magnetic disk, writable optical disk, etc.) and static memory (e.g., ROM, CD-ROM, etc.) for storing executable instructions that when executed perform the inventive steps described herein to controlling a set-top box based on device events. The memory 1505 also stores the data associated with or generated by the execution of the inventive steps.

While certain exemplary embodiments and implementations have been described herein, other embodiments and modifications will be apparent from this description.

Accordingly, the invention is not limited to such embodiments, but rather to the broader scope of the presented claims and various obvious modifications and equivalent arrangements.

What is claimed is:

1. A method comprising:
   detecting, by a sensor platform, a group of sensors,
      at least one sensor of the group of sensors outputting data in a format different from other sensors of the group of sensors;
   identifying, by the sensor platform, one or more gateway devices and a user account;
   associating, by the sensor platform, the at least one sensor with the one or more gateway devices;
   associating, by the sensor platform, the user account with the group of sensors or the one or more gateway devices;
   communicating, by the sensor platform, one or more associations, of the user account with the group of sensors or the one or more gateway devices, to a gateway device of the one or more gateway devices corresponding to the user account;
   receiving, by the sensor platform, first data in various formats from the group of sensors and the one or more gateway devices,
   the first data being pooled together as a collective data set;
   providing, by the sensor platform, trend analysis of the collective data set;
   converting, by the sensor platform, one or more of the first data, in the various formats, to a common format that can be utilized by a plurality of applications;
   receiving, by the sensor platform, a signal from a sensor device,
   the sensor device not being a member of the group of sensors;
   associating, by the sensor platform, the sensor device with the user account and the gateway device based on receiving the signal,
      the sensor device being enabled to exchange data with one or more sensors of the group of sensors;
   receiving, by the sensor platform, second data from the sensor device; and
   converting, by the sensor platform, the second data to the common format to be compatible with the plurality of applications.

2. The method according to claim 1, further comprising:
   detecting an indirect sensor;
   installing an interfacing software in the indirect sensor; and
   selectively registering the indirect sensor.

3. The method according to claim 1, further comprising:
   installing an interfacing software in the one or more gateway devices; and
   registering the one or more gateway devices.

4. The method according to claim 1, wherein the group of sensors are located within a personal area network.

5. The method according to claim 1, where receiving the first data in the various formats from the group of sensors and the one or more gateway devices comprises:
   receiving the first data in the various formats from an indirect sensor and the one more gateway devices.

6. A method comprising:
   detecting, by a sensor platform, a group of sensors,
      at least one sensor of the group of sensors outputting data in a format different from other sensors of the group of sensors;
   identifying, by the sensor platform, a user account;
   associating, by the sensor platform, the user account with the group of sensors;
   communicating, by the sensor platform, one or more associations, of the user account with the group of sensors, to a gateway device corresponding to the user account;
   receiving, by the sensor platform, first data in various formats from the group of sensors,
   the first data in the various formats being pooled together as a collective data set; and
   providing, by the sensor platform, trend analysis of the collective data set;
   converting, by the sensor platform, the first data, in the various formats, to a common format that can be utilized by a plurality of applications;
   receiving, by the sensor platform, a signal from a sensor device,
      the sensor device not being a member of the group of sensors;
   associating, by the sensor platform, the sensor device with the user account and the gateway device based on receiving the signal,
      the sensor device being enabled to exchange data with one or more sensors of the group of sensors;
   receiving, by the sensor platform, second data from the sensor device; and
   converting, by the sensor platform, the second data to the common format to be compatible with the plurality of applications.

7. The method according to claim 6, further comprising:
   detecting direct sensors of the group of sensors;
   selectively registering the direct sensors;
   installing an interfacing software into the direct sensors; and
   collecting data in the various formats from the direct sensors.

8. The method according to claim 6, further comprising:
   designating each of a plurality of agents to process the collective data set for trend analysis,
      the plurality of agents being configured to communicate with other agents within a personal area network through a policy engine.

9. The method according to claim 8, further comprising:
   determining one or more characteristics of at least one of the first data in the various formats or the plurality of agents; and
   determining one or more access rules, based on the one or more characteristics, for communication among the plurality of agents to program the policy engine.

10. The method according to claim 8, further comprising:
    receiving, from the plurality of agents, respective access settings associated with the plurality of agents for the policy engine; and
    creating an interface to facilitate communication among the plurality of agents based on the respective access settings.

11. The method according to claim 6, where receiving the first data in the various formats comprises:
    receiving the first data, in the various formats, from direct sensors of the group of sensors; and
    where the method further comprises:
       forwarding the first data, in the common format, to a direct actuator.

12. A sensor platform, comprising:
at least one processor; and
at least one memory, including computer program code for one or more programs that, when executed by the at least one processor, causes the at least one processor to:
  detect a group of sensors,
    at least one sensor of the group of sensors outputting data in a format different from other sensors of the group of sensors;
  identify one or more gateway devices and a user account;
  associate the at least one sensor with the one or more gateway devices,
  associate the user account with the group of sensors or the one or more gateway devices;
  communicate one or more associations, of the user account with the group of sensors or the one or more gateway devices, to a gateway device of the one or more gateway devices corresponding to the user account;
  receive first data in various formats from the group of sensors and the one or more gateway devices,
    the first data in the various formats being pooled together as a collective data set,
  provide trend analysis of the collective data set,
  convert the first data in the various formats to a common format that can be utilized by a plurality of applications;
  receive a signal from a sensor device,
    the sensor device not being a member of the group of sensors;
  associate the sensor device with the user account and the gateway device based on receiving the signal,
    the sensor device being enabled to exchange data with one or more sensors of the group of sensors;
  receive second data from the sensor device; and
  convert the second data to the common format to be compatible with the plurality of applications.

13. The sensor platform of claim 12, wherein the at least one processor is further to:
  detect an indirect sensor;
  install an interfacing software in the indirect sensor; and
  selectively register the indirect sensor.

14. The sensor platform of claim 12, wherein the at least one processor is further to:
  install an interfacing software in the one or more gateway devices; and
  register the one or more gateway devices.

15. The sensor platform of claim 12, wherein the at least one processor is further to:
  determine the at least one sensor is inactive; and
  remove the at least one sensor from a personal area network based on determining the at least one sensor is inactive.

16. The sensor platform of claim 12, wherein each sensor, of the group of sensors, is enabled to exchange data with at least one other sensor of the group of sensors.

17. A sensor platform, comprising:
at least one processor; and
at least one memory, including computer program code for one or more programs that, when executed by the at least one processor, cause the at least one processor to:
  detect a group of sensors,
    at least one sensor of the group of sensors outputting data in a format different from other sensors of the group of sensors,
  identify a user account,
  associate the user account with the group of sensors,
  communicate one or more associations, of the user account with the group of sensors, to a gateway device corresponding to the user account,
  receive first data in various formats from the group of sensors,
    the first data being pooled together as a collective data set,
  provide trend analysis of the collective data set,
  convert the first data to a common format that can be utilized by a plurality of applications,
  receive a signal from a sensor device,
    the sensor device not being a member of the group of sensors,
  associate the sensor device with the user account and the gateway device based on receiving the signal,
    the sensor device being enabled to exchange data with one or more sensors of the group of sensors,
  receive second data from the sensor device, and
  convert the second data to the common format to be compatible with the plurality of applications.

18. The sensor platform of claim 17, wherein the at least one processor is further to:
  detect direct sensors;
  selectively register the direct sensors;
  install an interfacing software into the direct sensors; and
  collect data in various formats from the direct sensors.

19. The sensor platform of claim 17, wherein the at least one processor is further to:
  designate each of a plurality of agents to process the collective data set for trend analysis,
    the plurality of agents being configured to communicate with other agents within a personal area network through a policy engine.

20. The sensor platform of claim 19, wherein the at least one processor is further to:
  determine one or more characteristics of at least one of the first data or the plurality of agents; and
  determine one or more access rules, based on the one or more characteristics, for communication among the plurality of agents to program the policy engine.

21. The sensor platform of claim 19, wherein the at least one processor is further to:
  receive, from the plurality of agents, respective access settings associated with the plurality of agents for the policy engine; and
  create an interface to facilitate communication among the plurality of agents based on the respective access setting.

22. The sensor platform of claim 17, wherein the at least one processor, when receiving the first data in the various formats from the group of sensors, are to:
  receive the first data in the various formats from direct sensors.

* * * * *